(12) United States Patent
Stamos et al.

(10) Patent No.: US 12,203,107 B2
(45) Date of Patent: Jan. 21, 2025

(54) NON-LTR-RETROELEMENT REVERSE TRANSCRIPTASE AND USES THEREOF

(71) Applicant: BOARD OF REGENTS, THE UNIVERSITY OF TEXAS SYSTEM, Austin, TX (US)

(72) Inventors: Jennifer L. Stamos, Austin, TX (US); Alfred M. Lentzsch, Austin, TX (US); Seung Kuk Park, Austin, TX (US); Georg Mohr, Austin, TX (US); Alan M. Lambowitz, Austin, TX (US)

(73) Assignee: BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 297 days.

(21) Appl. No.: 17/741,437

(22) Filed: May 10, 2022

(65) Prior Publication Data

US 2022/0372453 A1    Nov. 24, 2022

Related U.S. Application Data

(62) Division of application No. 16/753,201, filed as application No. PCT/US2018/054147 on Oct. 3, 2018, now Pat. No. 11,352,611.

(60) Provisional application No. 62/567,504, filed on Oct. 3, 2017.

(51) Int. Cl.
| C12N 9/12 | (2006.01) |
| C30B 7/00 | (2006.01) |
| C30B 29/58 | (2006.01) |
| G16B 15/00 | (2019.01) |

(52) U.S. Cl.
CPC ............ *C12N 9/1276* (2013.01); *C30B 29/58* (2013.01); *G16B 15/00* (2019.02); *C07K 2299/00* (2013.01); *C12Y 207/07049* (2013.01)

(58) Field of Classification Search
None
See application file for complete search history.

(56) References Cited

U.S. PATENT DOCUMENTS

| 7,670,807 B2 | 3/2010 | Lampson et al. |
| 9,333,946 B2 | 5/2016 | Simon |
| 2016/0289652 A1 | 10/2016 | Lambowitz et al. |

OTHER PUBLICATIONS

Adams, Paul D., et al. "Phenix: a comprehensive Python-based system for macromolecular structure solution." *Acta Crystallographica Section D: Biological Crystallography* 66.2 (2010): 213-221.

Aizawa, Yasunori, et al. "The pathway for DNA recognition and RNA integration by a group II intron retrotransposon." *Molecular cell* 11.3 (2003): 795-805.

Appleby, Todd C., et al. "Structural basis for RNA replication by the hepatitis C virus polymerase." *Science* 347.6223 (2015): 771-775.

Arnold, Jamie J., et al. "Remote Site Control of an Active Site Fidelity Checkpoint in a ViralRNA-dependent RNAPolymerase." *Journal of Biological Chemistry* 280.27 (2005): 25706-25716.

Blocker, Forrest JH, et al. "Domain structure and three-dimensional model of a group II intron-encoded reverse transcriptase." *RNA* 11.1 (2005): 14-28.

Branden, Carl Ivar, and John Tooze. *Introduction to protein structure*. $2^{nd}$ Ed. Garland Publishing Inc., New York, 1999.

Carignani, Giovanna, et al. "An mRNA maturase is encoded by the first intron of the mitochondrial gene for the subunit I of cytochrome oxidase in *S. cerevisiae.*" *Cell* 35.3 (1983): 733-742.

Cavalier-Smith, T. "Intron phylogeny: a new hypothesis." *Trends in Genetics* 7.5 (1991): 145-148.

Clark, Wesley C., et al. "tRNA base methylation identification and quantification via high-throughput sequencing." *Rna* 22.11 (2016): 1771-1784.

Costa, Maria, et al. "Crystal structures of a group II intron lariat primed for reverse splicing." *Science* 354.6316 (2016).

Cousineau, Benoit, et al. "Retrohoming of a bacterial group II intron: mobility via complete reverse splicing, independent of homologous DNA recombination." *Cell* 94.4 (1998): 451-462.

Das, Kalyan, et al. "Structures of HIV-1 RT-RNA/DNA ternary complexes with dATP and nevirapine reveal conformational flexibility of RNA/DNA: insights into requirements for RNase H cleavage." *Nucleic acids research* 42.12 (2014): 8125-8137.

Drenth, Jan. *Principles of protein X-ray crystallography*. Springer, New York, 1995.

Emsley, Paul, et al. "Features and development of Coot." *Acta Crystallographica Section D: Biological Crystallography* 66.4 (2010): 486-501.

Evans, Philip R., and Garib N. Murshudov. "How good are my data and what is the resolution ?." *Acta Crystallographica Section D: Biological Crystallography* 69.7 (2013): 1204-1214.

Feiten, Mirian Cristina, et al. "X-ray crystallography as a tool to determine three-dimensional structures of commercial enzymes subjected to treatment in pressurized fluids." *Applied biochemistry and biotechnology* 182 (2017): 429-451.

Fica, Sebastian M., et al. "RNA catalyses nuclear pre-mRNA splicing." *Nature* 503.7475 (2013): 229-234.

Fisher et al. "Substitutions at Phe61 in the beta3-beta4 hairpin of HIV-1 reverse transcriptase reveal a role for the Fingers subdomain in strand displacement DNA synthesis." *J Mol Biol.* Jan. 17, 2003;325(3):443-59.

(Continued)

*Primary Examiner* — Suzanne M Noakes
*Assistant Examiner* — Jae W Lee
(74) *Attorney, Agent, or Firm* — Parker Highlander PLLC

(57) ABSTRACT

A crystal structure of a Non-LTR-retroelement reverse transcriptase and methods of using the same to identify enzymes with improved activity are provided. Mutant reverse transcriptase enzymes and methods of using the same are also provided.

21 Claims, 17 Drawing Sheets
(12 of 17 Drawing Sheet(s) Filed in Color)
Specification includes a Sequence Listing.

(56) References Cited

OTHER PUBLICATIONS

Galej, Wojciech P., et al. "Crystal structure of Prp8 reveals active site cavity of the spliceosome." *Nature* 493.7434 (2013): 638-643.
Galej, Wojciech P., et al. "Structural studies of the spliceosome: zooming into the heart of the machine." *Current opinion in structural biology* 25 (2014): 57-66.
Gao, Guangxia, et al. "Conferring RNA polymerase activity to a DNA polymerase: a single residue in reverse transcriptase controls substrate selection." *Proceedings of the National Academy of Sciences* 94.2 (1997): 407-411.
Gillis, Andrew J., Anthony P. Schuller, and Emmanuel Skordalakes. "Structure of the Tribolium castaneum telomerase catalytic subunit TERT." *nature* 455.7213 (2008): 633-637.
Huang, Huifang, et al. "Structure of a covalently trapped catalytic complex of HIV-1 reverse transcriptase: implications for drug resistance." *Science* 282.5394 (1998): 1669-1675.
International Preliminary Report on Patentability issued in International Application No. PCT/US2018/054147, dated Apr. 16, 2020.
International Search Report and Written Opinion issued in International Application No. PCT/US2018/054147, dated Feb. 19, 2019.
Kabsch, W. (2010). "XDS." *Acta Crystallogr. D Biol. Crystallogr.* 66, 125-132.
Kennell, John C., et al. "Reverse transcriptase activity associated with maturase-encoding group II introns in yeast mitochondria." *Cell* 73.1 (1993): 133-146.
Kierzek, A M, and P Zielenkiewicz. "Models of protein crystal growth." *Biophysical chemistry* vol. 91,1 (2001): 1-20.
Kissinger, Charles R., Daniel K. Gehlhaar, and David B. Fogel. "Rapid automated molecular replacXement by evolutionary search." *Acta Crystallographica Section D: Biological Crystallography* 55.2 (1999): 484-491.
Koonin, Eugene V., Valerian V. Dolja, and Mart Krupovic. "Origins and evolution of viruses of eukaryotes: the ultimate modularity." *Virology* 479 (2015): 2-25.
Lambowitz, Alan M., and Marlene Belfort. "Mobile bacterial group II introns at the crux of eukaryotic evolution." *Microbiology spectrum* 3.1 (2015): 3-1.
Lambowitz, Alan M., and Steven Zimmerly. "Group II introns: mobile ribozymes that invade DNA." *Cold Spring Harbor perspectives in biology* 3.8 (2011): a003616.
Malik, Harmit S., William D. Burke, and Thomas H. Eickbush. "The age and evolution of non-LTR retrotransposable elements." *Molecular biology and evolution* 16.6 (1999): 793-805.
Marcia, Marco, and Anna Marie Pyle. "Visualizing group II intron catalysis through the stages of splicing." *Cell* 151.3 (2012): 497-507.
Martin, William, and Eugene V. Koonin. "Introns and the origin of nucleus-cytosol compartmentalization." *Nature* 440.7080 (2006): 41-45.
McPherson, Alexander, and Jose A Gavira. "Introduction to protein crystallization." *Acta crystallographica. Section F, Structural biology communications* vol. 70,Pt 1 (2014): 2-20.
Michel, François, and Jean-Luc Ferat. "Structure and activities of group II introns." *Annual review of biochemistry* 64.1 (1995): 435-461.
Mitchell, Meghan, et al. "Structural basis for telomerase catalytic subunit TERT binding to RNA template and telomeric DNA." *Nature structural & molecular biology* 17.4 (2010): 513-518.
Mohr, Sabine, et al. "Thermostable group II intron reverse transcriptase fusion proteins and their use in cDNA synthesis and next-generation RNA sequencing." *Rna* 19.7 (2013): 958-970.
Murshudov, Garib N., et al. "REFMAC5 for the refinement of macromolecular crystal structures." *Acta Crystallographica Section D: Biological Crystallography* 67.4 (2011): 355-367.

Nguyen, Thi Hoang Duong, et al. "CryoEM structures of two spliceosomal complexes: starter and dessert at the spliceosome feast." *Current opinion in structural biology* 36 (2016): 48-57.
Noah, James W., et al. "Atomic force microscopy reveals DNA bending during group II intron ribonucleoprotein particle integration into double-stranded DNA." *Biochemistry* 45.41 (2006): 12424-12435.
Nottingham, Ryan M., et al. "RNA-seq of human reference RNA samples using a thermostable group II intron reverse transcriptase." *Rna* 22.4 (2016): 597-613.
Paukstelis, Paul J., et al. "Structure of a tyrosyl-tRNA synthetase splicing factor bound to a group I intron RNA." *Nature* 451.7174 (2008): 94-97.
Peebles, Craig L., et al. "A self-splicing RNA excises an intron lariat." *Cell* 44.2 (1986): 213-223.
Qu, Guosheng, et al. "Structure of a group II intron in complex with its reverse transcriptase." *Nature structural & molecular biology* 23.6 (2016): 549-557.
Saldanha, Roland, et al. "RNA and protein catalysis in group II intron splicing and mobility reactions using purified components." *Biochemistry* 38.28 (1999): 9069-9083.
San Filippo, Joseph, and Alan M. Lambowitz. "Characterization of the C-terminal DNA-binding/DNA endonuclease region of a group II intron-encoded protein." *Journal of molecular biology* 324.5 (2002): 933-951.
Sawaya, Michael R., et al. "Crystal structures of human DNA polymerase β complexed with gapped and nicked DNA: evidence for an induced fit mechanism." *Biochemistry* 36.37 (1997): 11205-11215.
Sharp, Phillip A. "On the origin of RNA splicing and introns." *Cell* 42.2 (1985): 397-400.
Sontheimer, Erik J., Peter M. Gordon, and Joseph A. Piccirilli. "Metal ion catalysis during group II intron self-splicing: parallels with the spliceosome." *Genes & development* 13.13 (1999): 1729-1741.
Stamos, Jennifer L., Alfred M. Lentzsch, and Alan M. Lambowitz. "Structure of a thermostable group II intron reverse transcriptase with template-primer and its functional and evolutionary implications." *Molecular Cell* 68.5 (2017): 926-939.
Toro, Nicolás, and Rafael Nisa-Martínez. "Comprehensive phylogenetic analysis of bacterial reverse transcriptases." *PLoS One* 9.11 (2014): e114083.
Wang, He, and Alan M. Lambowitz. "The Mauriceville plasmid reverse transcriptase can initiate cDNA synthesis de novo and may be related to reverse transcriptase and DNA polymerase progenitor." *Cell* 75.6 (1993): 1071-1081.
Wu, Xuebing, and David P. Bartel. "Widespread influence of 3'-end structures on mammalian mRNA processing and stability." *Cell* 169.5 (2017): 905-917.
Yang, Jian, et al. "Efficient integration of an intron RNA into double-stranded DNA by reverse splicing." *Nature* 381.6580 (1996): 332-335.
Zhao, Chen, and Anna Marie Pyle. "Crystal structures of a group II intron maturase reveal a missing link in spliceosome evolution." *Nature Structural & Molecular Biology* 23.6 (2016): 558-565.
Zheng, Guanqun, et al. "Efficient and quantitative high-throughput tRNA sequencing." *Nature methods* 12.9 (2015): 835-837.
Zimmerly, Steven, and Li Wu. "An unexpected diversity of reverse transcriptases in bacteria." *Microbiology spectrum* 3.2 (2015): 3-2.
Zimmerly, Steven, et al. "A group II intron RNA is a catalytic component of a DNA endonuclease involved in intron mobility." *Cell* 83.4 (1995): 529-538.
Zimmerly, Steven, et al. "Group II intron mobility occurs by target DNA-primed reverse transcription." *Cell* 82.4 (1995): 545-554.
Zubradt, Meghan, et al. "DMS-MaPseq for genome-wide or targeted RNA structure probing in vivo." *Nature methods* 14.1 (2017): 75-82.

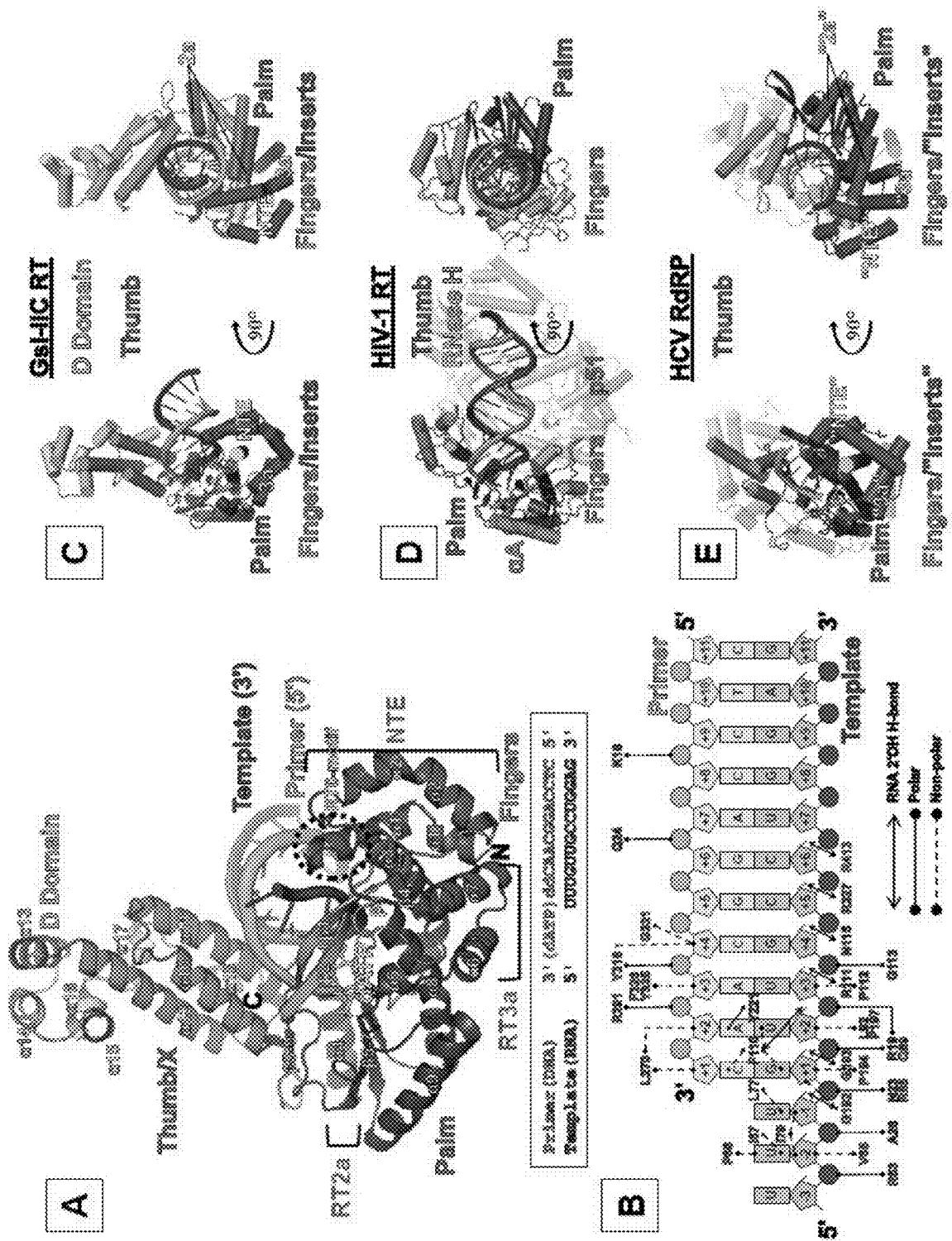
FIGS. 2A-E

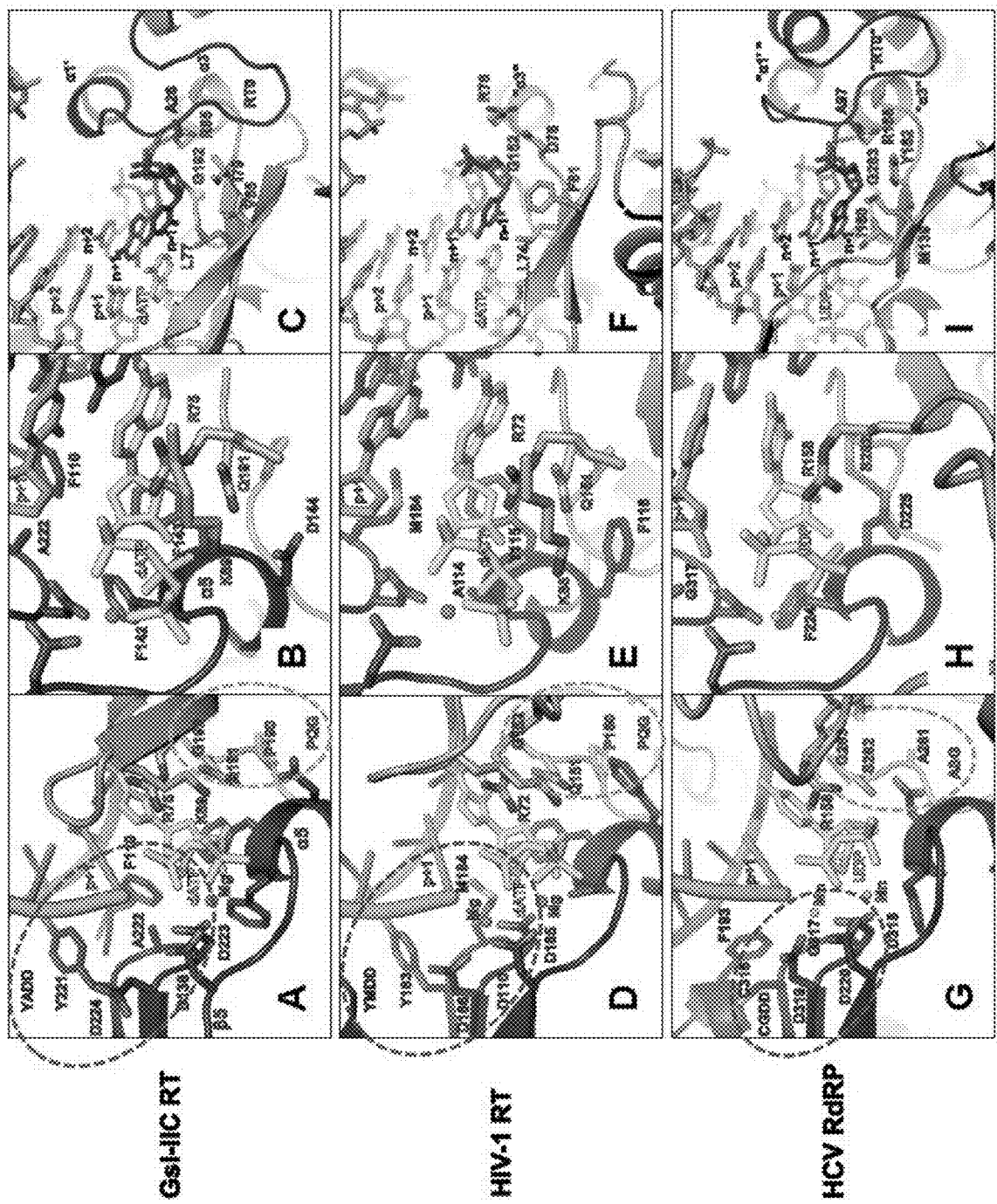
FIGS. 3A-I

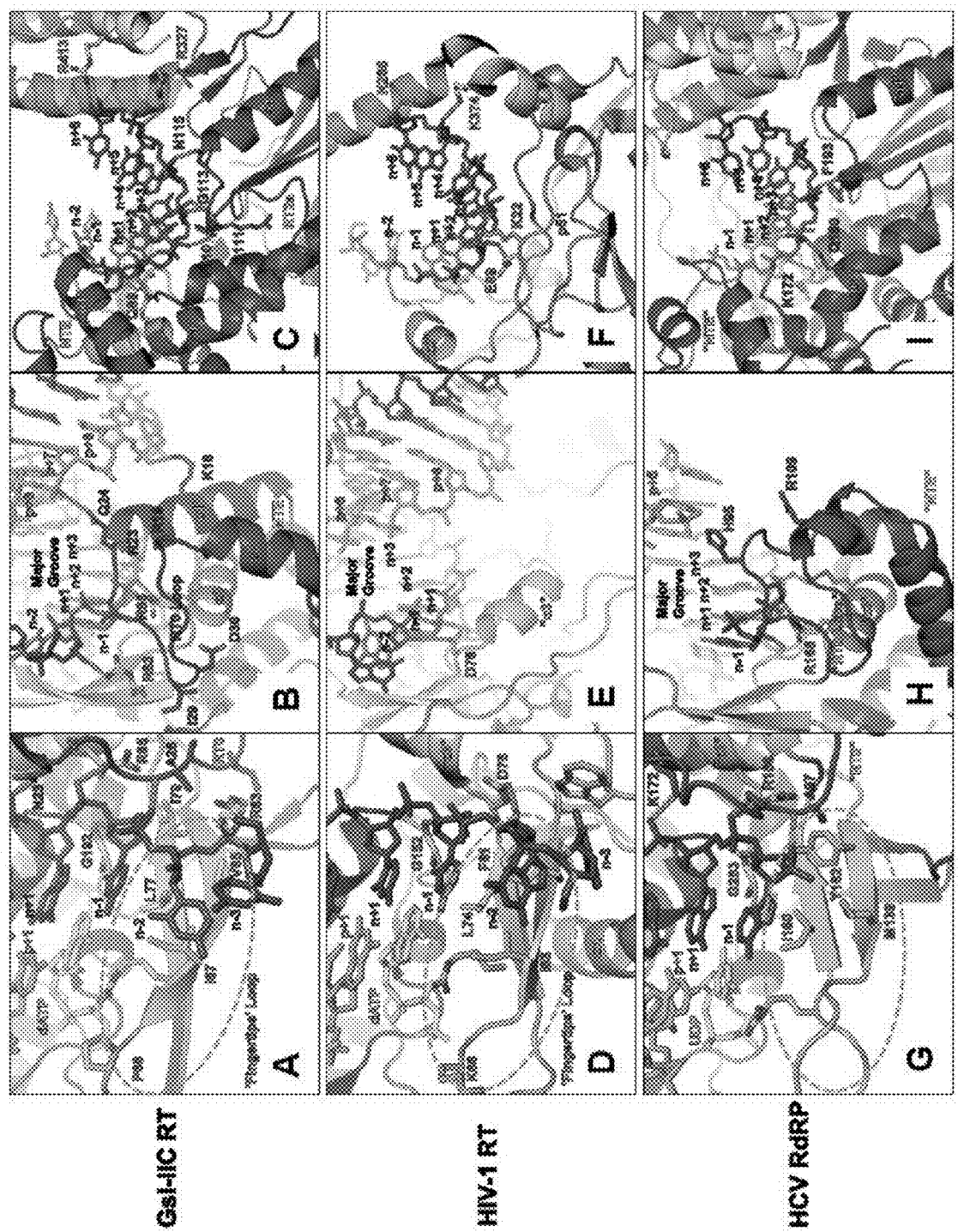
FIGS. 4A-I

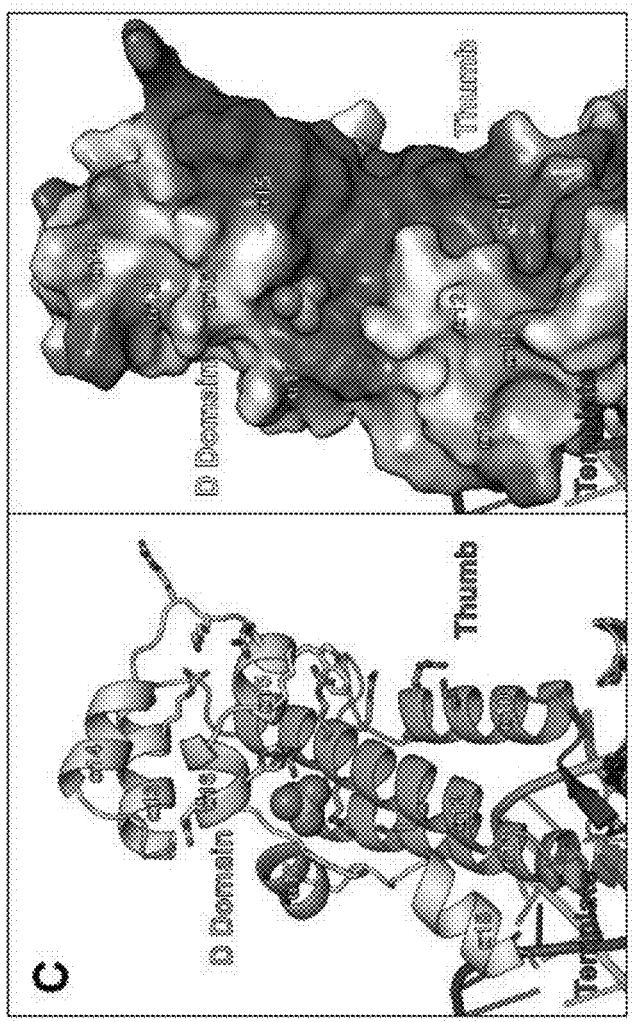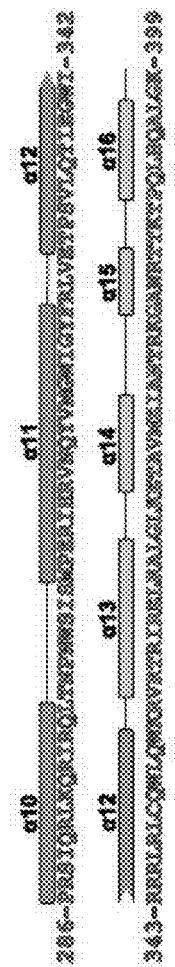
FIGS. 5A-C

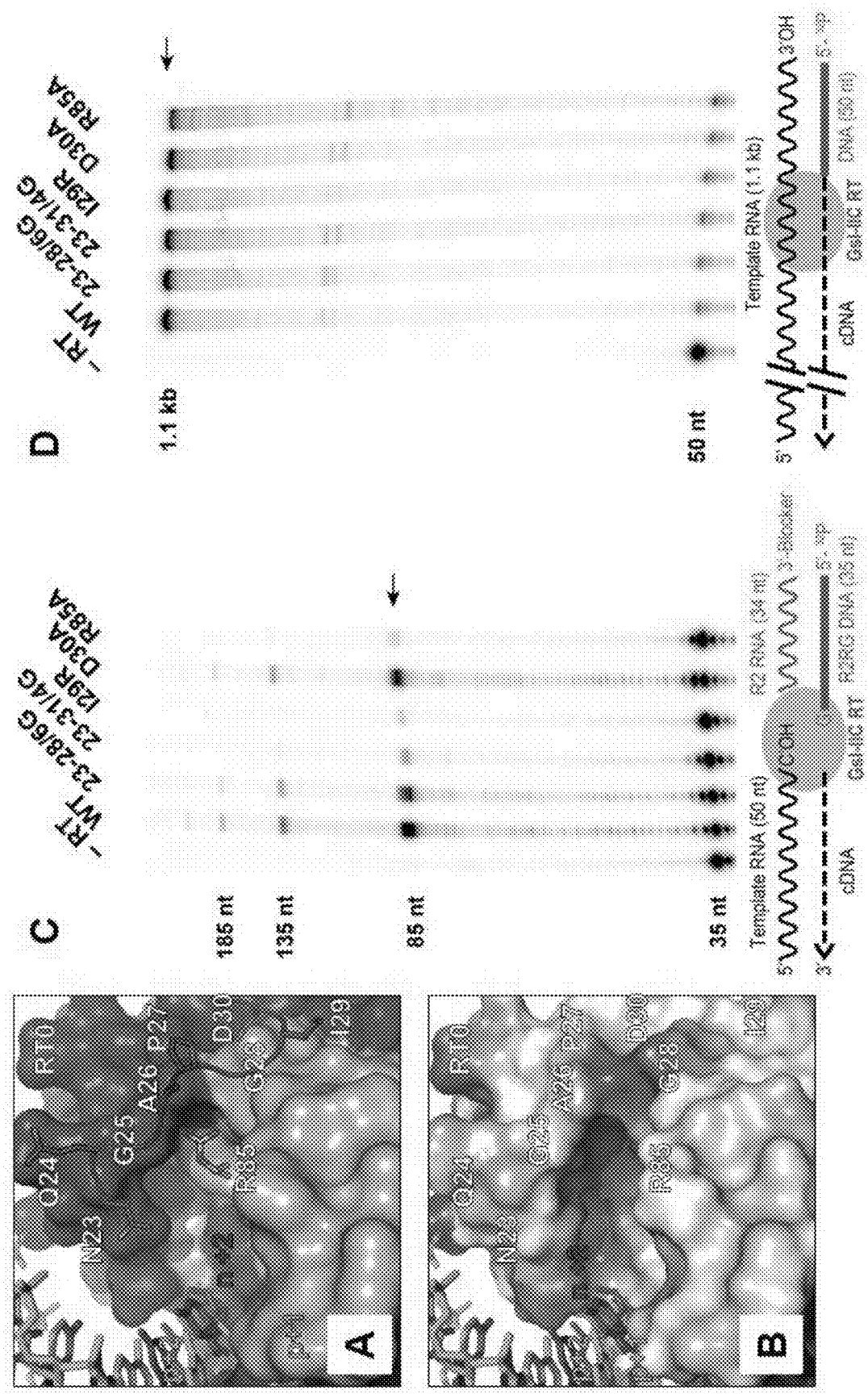
FIGS. 6A-D

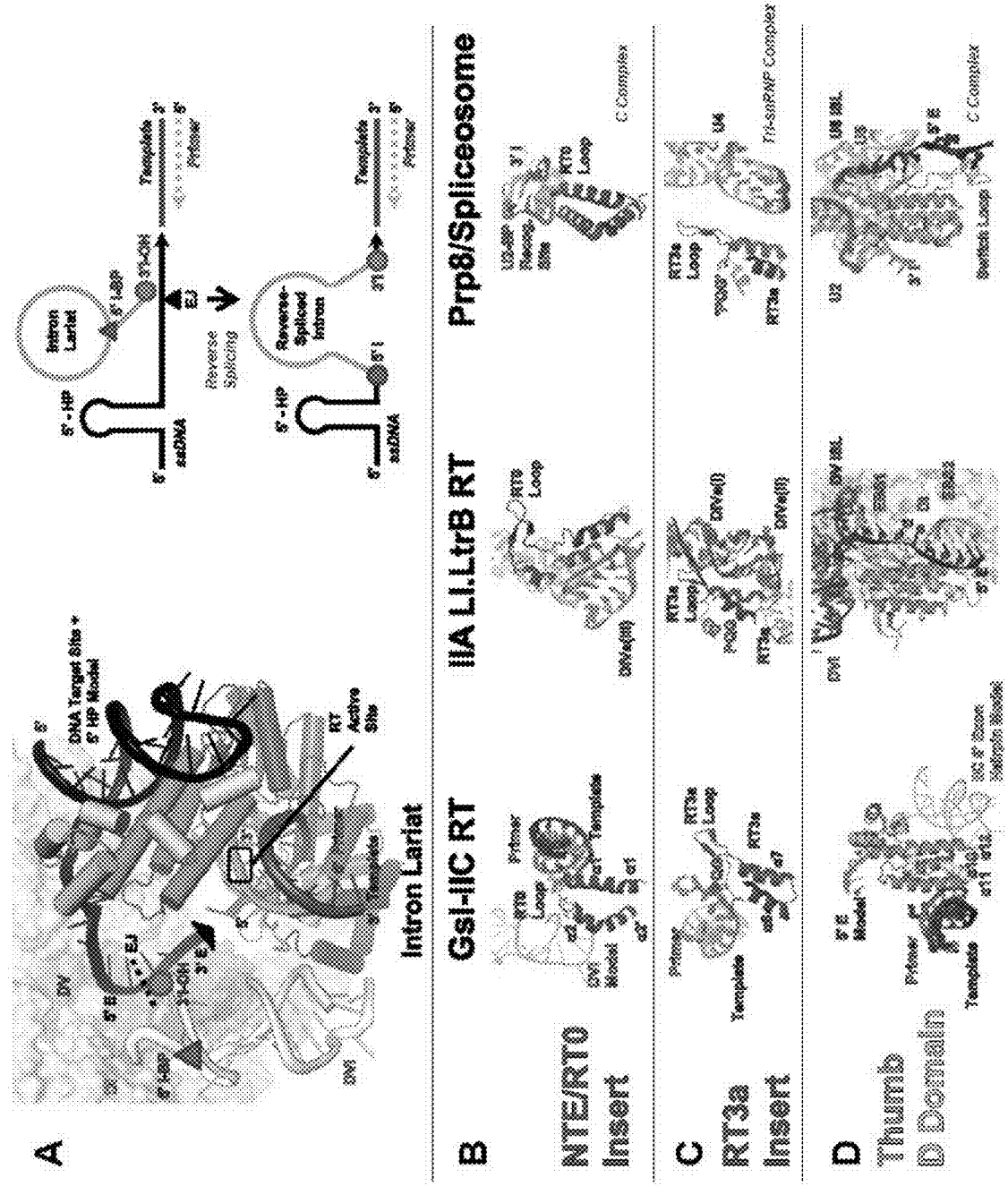
FIGS. 7A-D

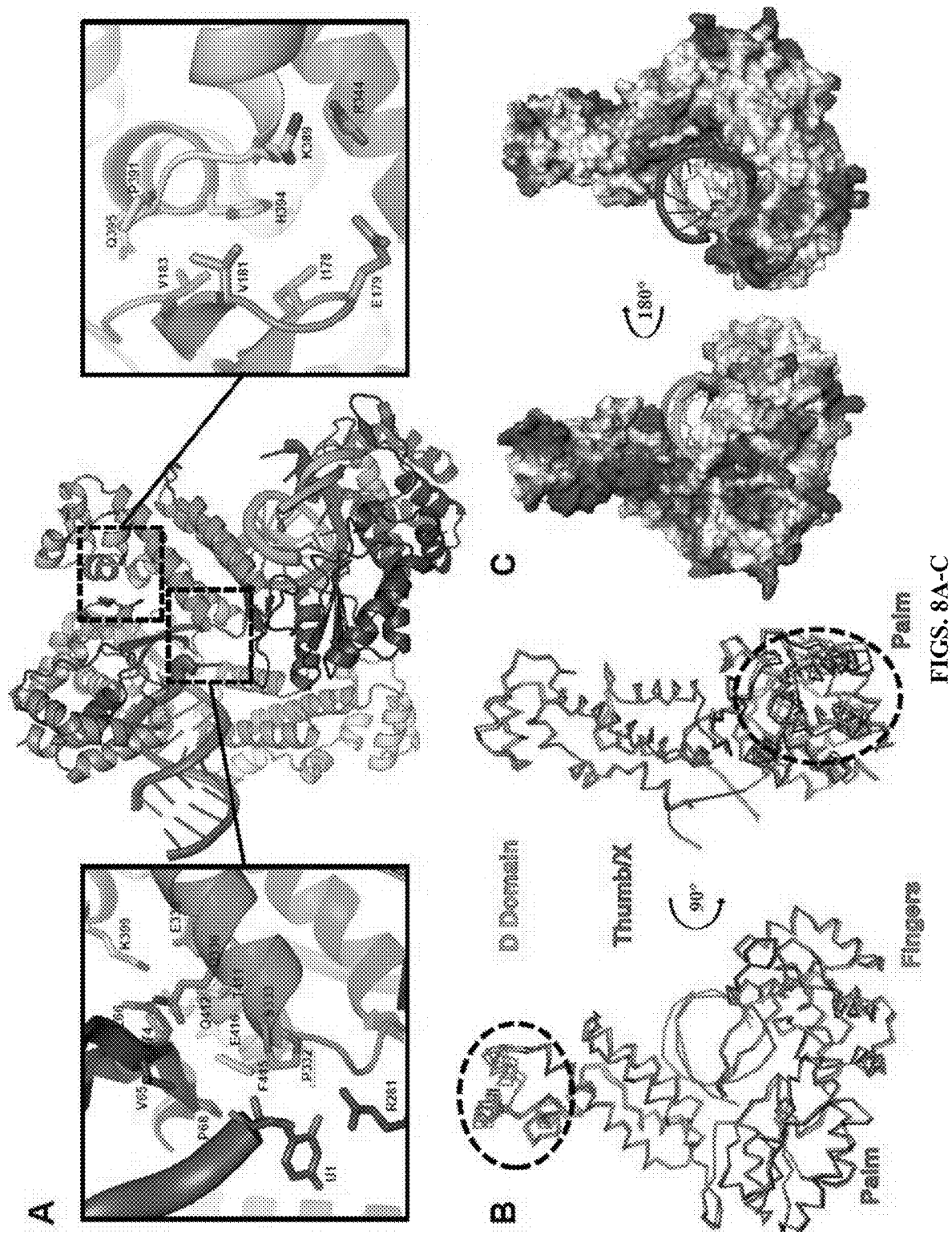
FIGS. 8A-C

```
                    RT0 Loop
                 ┌──────────┐
  1 MALLERILARDNLITALKRVEA NQGAPGIDG VSTDQLRD  39
                            RT1
 40 YIRAHWSTIHAQLLAGTYRPAPVRRVEIPKPGGGTRQLG   78
       RT2                         RT2a
 79 IPTVVDRLIQQAILQELTPIFDPDFSSSSFGFRPGRNAH  117
                       RT3
118 DAVRQAQGYIQEGYRYVVDMDLEKFFDRVNHDILMSRVA  156
         RT3a
157 RKVKDKRVLKLIRAYLQAGVMIEGVKVQTEEGTPQGGPL  195
                 RT4                   RT5
196 SPLLANILLDDLDKELEKRGLKFCRYADDCNIYVKSLRA  234
              RT6                      RT7
235 GQRVKQSIQRFLEKTLKLKVNEEKSAVDRPWKRAFLGFS  273
274 FTPERKARIRLAPRSIQRLKQRIRQLTNPNWSISMPERI  312
                     Thumb
313 HRVNQYVMGWIGYFRLVETPSVLQTIEGWIRRRLRLCQW  351
                         DNA Binding Domain (?)
352 LQWKRVRTRIRELRALGLKETAVMEIANTRKGAWRTTKT  390
391 PQLHQALGKTYWTAQGLKSLTQRYFELRQG          420
```

NON-LTR-RETROELEMENT REVERSE TRANSCRIPTASE AND USES THEREOF

The present application is a divisional of U.S. patent application Ser. No. 16/753,201, filed Apr. 2, 2020, now U.S. Pat. No. 11,352,611, which is as a national phase application under 35 U.S.C. § 371 of International Application No. PCT/US2018/054147, filed Oct. 3, 2018, which claims the priority benefit of U.S. Provisional Patent Application No. 62/567,504, filed Oct. 3, 2017, the entire contents of each of which are incorporated herein by reference.

The invention was made with government support under Grant Nos. RO1 GM037949 and GM037951 awarded by the National Institutes of Health. The government has certain rights in the invention.

BACKGROUND OF THE INVENTION

1. Field of the Invention

The present invention relates generally to the field of molecular biology and biochemistry. More particularly, it concerns non-LTR-retroelement reverse transcriptase enzymes (RTs), which include non-LTR-retrotransposon RTs, bacterial RTs, and group II intron RTs. Non-LTR-retroelement RTs are characterized by a larger fingers region than retroviral RTs. This larger fingers region typically contains a distinctive N-terminal extension (NTE), often with a conserved sequence element RT0, and at least two distinctive insertions, denoted RT2a and RT3a, between conserved RT sequence blocks RT1-7 found in all RTs. Examples of non-LTR-retroelement RTs are given in Malik et al., 1999; Blocker et al., 2005; Toro and Nisa-Martínez, 2014; and Zimmerly and Wu, 2015, and are incorporated herein by reference.

2. Description of Related Art

Non-LTR-retroelement reverse transcriptase enzymes (RTs) have to date been the subject of much less study than retroviral RTs. For instance, mobile group II introns are bacterial retrotransposons, which are closely related to the evolutionary ancestors of spliceosomal introns, the spliceosome, non-LTR-retrotransposons, telomerase, and retroviruses in eukaryotes (Lambowitz and Belfort, 2015). They are comprised of an autocatalytic intron RNA (a "ribozyme") and a distinct species of intron-encoded RT (Lambowitz and Zimmerly, 2011). The intron RNA catalyzes its own excision from a precursor RNA by RNA splicing reactions identical to those of eukaryotic spliceosomal introns (Fica et al., 2013; Peebles et al., 1986; Sontheimer et al., 1999), while the intron-encoded RT functions both as an RNA splicing co-factor and to promote intron mobility to new genomic DNA sites (Carignani et al., 1983; Kennell et al., 1993; Saldanha et al., 1999). The latter occurs by a process called retrohoming in which the excised intron RNA inserts ("reverse splices") directly into a DNA site and is reverse transcribed by the RT to produce an intron cDNA integrated into the genome (Cousineau et al., 1998; Yang et al., 1996; Zimmerly et al., 1995a; Zimmerly et al., 1995b).

Mobile group II intron RTs are homologous to well-studied retroviral RTs but have key structural and functional differences, reflecting their different biological functions (Mohr et al., 2013). While error prone and poorly processive retroviral RTs evolved to help retroviruses evade host defenses, group II intron RTs evolved to faithfully reverse transcribe a long, highly structured intron RNA (Lambowitz and Belfort, 2015). As a result, group II intron RTs have higher fidelity, processivity and strand displacement activity than retroviral RTs, along with a novel end-to-end template switching activity that is minimally dependent upon base pairing (Mohr et al., 2013). Recently, new methods for producing group II intron RTs in soluble form with high yield and activity have enabled their use for biotechnological applications, including new approaches for next-generation RNA sequencing (RNA- seq), identification of RNA post-transcriptional modifications, and RNA structure mapping (Clark et al., 2016; Nottingham et al., 2016; Wu and Bartel, 2017; Zheng et al., 2015; Zubradt et al., 2016).

An evolutionary relationship between group II and spliceosomal introns was first suggested by their similar splicing mechanisms and by the ability of group II intron RNAs to be fragmented into functional segments that can reassociate to promote RNA splicing analogous to the function of snRNAs in eukaryotes (Sharp, 1985). Together with their phylogenetic distribution, these findings suggested a scenario in which mobile group II introns evolved in bacteria, entered ancestral eukaryotes with bacterial endosymbionts that gave rise to mitochondria and chloroplasts, invaded the nucleus, proliferated to high copy number, and then degenerated into spliceosomal introns, with group II intron RNA domains evolving into snRNAs that reconstitute to form the spliceosome (Cavalier-Smith, 1991; Martin and Koonin, 2006). Recent structural and biochemical studies have strongly supported this evolutionary relationship by showing that the core spliceosomal protein Prp8 likely evolved from a group II intron-like RT and functions similarly by acting as a protein scaffold for an RNA catalytic core composed of snRNAs that are structurally and functionally related to group II intron RNA domains (Galej et al., 2014; Nguyen et al., 2016).

Despite their biochemical, biotechnological, and evolutionary significance, high-resolution structural information about group II intron RTs has been lacking. Group II introns and their encoded RTs have evolved into the three main structural subgroups denoted IIA, IIB, and IIC (Lambowitz and Zimmerly, 2011; Michel and Ferat, 1995). However, there is an unmet need to elucidate the structural features that contribute to functions of the enzymes.

SUMMARY OF THE INVENTION

In a first embodiment of the present disclosure, there is provided a crystal comprising a substantially pure non-LTR-retroelement reverse transcriptase comprised of at least a reverse transcriptase and a thumb domain in complex with template and primer oligonucleotide and incoming dNTP. In some aspects, the non-LTR-retroelement reverse transcriptase is a bacterial reverse transcriptase, such as a group II intron reverse transcriptase or a thermostable reverse transcriptase. In some aspects, the incoming dNTP is dATP.

In certain aspects, the crystal has lattice constants of a=179.2 Å, b=95.1 Å, c=71.6 Å, α=90°, β=113.5°, γ=90°. In particular aspects, the crystal has a space group of C 1 2 1. In some aspects, the crystal has the crystal structure as defined in Table 1.

In some aspects, the non-LTR-retroelement reverse transcriptase has the amino acid sequence at least 85%, such as 86%, 87%, 88%, 89%, 90%, 91%, 92%, 93%, 94%, 95%, 96%, 97%, 98%, 99%, or 100%, identical to the reverse transcriptase and the thumb domains of the polypeptide of SEQ ID NO: 1. In particular aspects, the non-LTR-retroelement reverse transcriptase has the reverse transcriptase and a thumb domain of the polypeptide of SEQ ID NO: 1 (see, e.g., U.S. Pat. No. 7,670,807 and U.S. Pub. No. US2016/0289652A1, which are incorporated herein by reference).

In certain aspects, the non-LTR-retroelement reverse transcriptase has the amino acid sequence at least 85%, such as 86%, 87%, 88%, 89%, 90%, 91%, 92%, 93%, 94%, 95%, 96%, 97%, 98%, 99%, or 100%, identical to the polypeptide of SEQ ID NO: 1. In particular aspects, the non-LTR-retroelement reverse transcriptase has the amino acid sequence of the polypeptide of SEQ ID NO: 1.

In another embodiment, there is provided a tangible computer-readable media comprising the crystal structure constants of a crystal of the embodiments, such as a crystal comprising a substantially pure non-LTR-retroelement reverse transcriptase comprised of at least a reverse transcriptase and a thumb domain in complex with template and primer oligonucleotide and incoming dNTP. In particular aspects, the crystal has a resolution of about 3.0 Å.

Further embodiments provide a method for identifying a non-LTR-retroelement RT having an improved property, the method comprising obtaining a crystal of the embodiments (e.g., a crystal comprising a substantially pure non-LTR-retroelement reverse transcriptase comprised of at least a reverse transcriptase and a thumb domain in complex with template and primer oligonucleotide and incoming dNTP) or a tangible computer-readable media of the embodiments (e.g., a tangible computer-readable media comprising the crystal structure constants of a crystal of the embodiments); and identifying one or more residues of interest for amino acid substitution, deletion or insertion predicted to provide an improved property.

In additional aspects, the method further comprises expressing a nucleic acid encoding the identified non-LTR-retroelement RT to provide an enzyme having said improved property.

In yet another embodiment, there is provided a method of generating mutants of a non-LTR-retroelement RT with improved property comprising generating crystals of the embodiments; performing x-ray crystallography on the crystals; and identifying one or more residues of interest for amino acid substitution, deletion or insertion predicted to provide an improved enzymatic activity. In further aspects, the method further comprises generating mutants of a non-LTR-retroelement RT by mutating at least one residue of interest identified in the identifying step.

In some aspects, the non-LTR-retroelement RT is a bacterial reverse transcriptase. In some aspects, the RT is a group II intron reverse transcriptase. In some aspects, the non-LTR-retroelement RT is at least 50%, such as at least 60%, 70%, 80%, or 90%, identical to SEQ ID NO: 1.

In certain aspects, the residues of interest comprise a region of conservation. In specific aspects, the region of conservation comprises the fingertip motifs, such as V65, 179, P68, and/or R63. In certain aspects, the region of interest comprises the N-terminal extension (NTE). In particular aspects, the NTE comprises at least 1 alpha helix.

In some aspects, the at least one alpha helix comprises at least amino acids Q24 and K18. In certain aspects, the NTE comprises the RT0 region. In particular aspects, the RT0 region comprises the RT0 loop and/or R85. In some aspects, the RT0 loop comprises amino acids 23-31.

In certain aspects, the residues of interest are in the thumb domain, in the palm subdomain, in the D domain, in the amino acids contacting the major groove, in the amino acids contacting the minor groove, in the amino acids contacting the phosphodiester backbone, base, ribose or deoxyribose sugar, and/or in RT2a. In some aspects, the residues of interest comprise F110.

In some aspects, the method comprises identifying one or more residues of interest for amino acid substitution. In certain aspects, the substitution comprises replacing the amino acid with an amino acid of opposite charge, replacing the amino acid with an uncharged amino acid, replacing the amino acid with a charged amino acid, replacing the amino acid with a hydrophobic amino acid, replacing the amino acid with a proline, replacing the amino acid with a cysteine or selenocysteine, and/or replacing the amino acid with a glycine or alanine In additional aspects, the method further comprises expressing an enzyme comprising the substitution and evaluating the properties or activity of the enzyme.

In some aspects of any of the above embodiments, the improved property is an improved enzymatic activity. In certain aspects, the improved enzymatic activity comprises: increased or decreased template switching activity; increased or decreased processivity; increased or decreased strand displacement activity; or increased or decreased fidelity. In particular aspects, the improved enzymatic activity comprises: increased or decreased template switching activity; increased processivity; increased strand displacement activity; or increased fidelity.

In certain aspects of the above embodiments, the improved property comprises higher solubility, higher thermostability or decreased non-specific nucleic acid binding.

Further provided herein is a non-LTR-retroelement reverse transcriptase (RT) comprising, an amino acid substitution at an amino acid position corresponding to a position of SEQ ID NO: 1 that contacts a template nucleic acid, a primer oligonucleotide and/or an incoming dNTP. Another embodiment provides a non-LTR-retroelement reverse transcriptase (RT) comprising, an amino acid substitution at an amino acid position corresponding to a position of SEQ ID NO: 1 that is on the surface of the RT. Yet still a further embodiment provides a non-LTR-retroelement reverse transcriptase (RT) comprising, an amino acid substitution at an amino acid position corresponding to positions 18, 19, 21, 23, 24, 25, 26, 27, 28, 29, 30, 31, 32, 33, 63, 65, 67, 68, 69, 75, 77, 79, 85, 89, 92, 110, 111, 112, 113, 114, 115, 138, 139, 140, 141, 142, 143, 175, 176, 177, 178, 179, 180, 181, 182, 183, 184, 191, 192, 193, 194, 197, 221, 223, 255, 258, 270, 290, 291, 293, 294, 297, 298, 301, 303, 304, 305, 306, 307, 311, 317, 318, 321, 322, 324, 325, 326, 327, 343, 344, 345, 347, 353, 355, 356, 358, 360, 379, 380, 381, 382, 386, 389, 394, 399, 413 and/or 415 of SEQ ID NO: 1.

In several aspects, the RT comprises an amino acid substitution selected from the group consisting of: E21A, F415A, N301H, N301G, N303H, N303G, S305H, S305G, S307H, S307G, Q353R, R311L, R327L, R343L, R344L, R345L, R347L, Q353H, Q353R, K355D, K355G, R356L, R356G, R358A, R360A, N379A, T380A, K399D and H394A. In other aspects, the RT comprises an amino acid substitution selected from the group consisting of: replacing positions 23-33 with GGGG and replacing positions 175-184 with polyG.

In certain aspects, the RT comprises an amino acid substitution at a position corresponding to position 29, an amino acid substitution at a position corresponding to position 29 to an Arg residue, an amino acid substitution at a position corresponding to position 85, an amino acid substitution at a position corresponding to position 85 to an Ala residue, an amino acid substitution at a position corresponding to position 30, an amino acid substitution at a position corresponding to position 30 to an Ala residue, an amino acid substitution at a position corresponding to one of amino acids 23-31 to a Gly, and/or an amino acid substitution at a position corresponding to one of amino acids 23-28 to a Gly.

In some aspects, the RT comprises a bacterial reverse transcriptase, such as a group II intron reverse transcriptase. In certain aspects, the RT comprises an amino acid sequence at least 85%, such as 86%, 87%, 88%, 89%, 90%, 91%, 92%, 93%, 94%, 95%, 96%, 97%, 98%, 99%, or 100%, identical to SEQ ID NO: 1. In some aspects, the RT comprises: increased or decreased template switching activity; increased or decreased processivity; increased or decreased strand displacement activity; or increased or decreased fidelity. In certain aspects, the RT comprises increased or decreased template switching activity; increased processivity; increased strand displacement activity; or increased fidelity. In particular aspects, the RT comprises: higher solubility, higher thermostability or decreased non-specific nucleic acid binding. In several aspects, the RT exhibits increased yield during recombinant production. In additional aspects, the RT further comprises a stability tag. In a specific aspect, the stability tag comprises MalE.

In another embodiment, there is provided a non-LTR-retroelement reverse transcriptase (RT) comprising, an amino acid substitution at an amino acid position corresponding to positions 18, 19, 23, 24, 25, 26, 27 28, 29, 30, 31, 63, 65, 67, 68, 69, 75, 77, 79, 85, 89, 92, 110, 111, 112, 113, 114, 115, 138, 139, 140, 141, 142, 143, 191, 192, 193, 194, 197, 221, 223, 255, 258, 270, 290, 291, 293, 294, 297, 298, 304, 306, 317, 318, 321, 322, 324, 325, 326, 327, 381, 382, 386, 389 and/or 413 of SEQ ID NO: 1. Further aspects, a non-LTR-retroelement comprises an amino acid substitution at an amino acid position corresponding to positions 18, 19, 23, 24, 25, 26, 27 28, 29, 30, 31, 63, 67, 68, 69, 75, 77, 79, 85, 89, 92, 110, 111, 112, 113, 114, 115, 138, 139, 140, 141, 142, 143, 191, 192, 193, 194, 197, 221, 223, 255, 258, 270, 291, 317, 318, 321, 322, 324, 325, 326, 327 and/or 413 of SEQ ID NO: 1. In certain aspects, the RT comprises an amino acid substitution at a position corresponding to position 29, an amino acid substitution at a position corresponding to position 29 to an Arg residue, an amino acid substitution at a position corresponding to position 85, an amino acid substitution at a position corresponding to position 85 to an Ala residue, an amino acid substitution at a position corresponding to position 30, an amino acid substitution at a position corresponding to position 30 to an Ala residue, an amino acid substitution at a position corresponding to one of amino acids 23-31 to a Gly, and/or an amino acid substitution at a position corresponding to one of amino acids 23-28 to a Gly.

A further embodiment provides a method for reverse transcribing a template comprising contacting the template with a RT of the above embodiments in conditions permissible for reverse transcription. Also provided herein is a kit comprising a RT of the embodiments.

In yet another embodiment, there is provided a non-LTR-retroelement reverse transcriptase (RT) comprising, at least one amino acid substitution at an amino acid position corresponding to a position of SEQ ID NO: 1 that is positioned on the exterior of the protein, does not contact a template nucleic acid, a primer oligonucleotide and/or an incoming dNTP. In certain aspects, the RT further comprises at least one amino acid substitution in the thumb domain, the palm subdomain, the fingers subdomain, or the N-terminal extension. In some aspects, the at least one substitution is at an amino acid position conserved in other non-LTR-retroelement RTs. In specific aspects, the at least one substitution is at an amino acid position in the thumb domain. In certain aspects, the RT comprises an improved property, such as improved stability, improved solubility, decreased non-specific nucleic acid binding or improved ability to be purified.

In particular aspects, the at least one substitution is at an amino acid position selected from Q290, Q294, Q298, K293, R297, W304 and/or I306. In some aspects, the at least one substitution is at amino acid positions Q290, Q294 and Q300. In certain aspects, at least one substitution comprises Q290A, Q294A and Q298A. In particular aspects, the at least one substitution is at amino acid positions K293 and R297. In some aspects, the at least one substitution comprises K293A and R297A. In certain aspects, the at least one substitution is at amino acid positions W304 and I306. In some aspects, the at least one substitution comprises W304A and I306A. In one specific aspect, the at least one substitution is at an amino acid position in or in the D domain (positions 356 to 420 of SEQ ID NO: 1). In some aspects, the at least one substitution is at an amino acid position selected from R381, K382, R386 and/or K389. In certain aspects, the at least one substitution is at amino acid positions R381, K382, R386 and K389. In certain aspects, the at least one substitution comprises R381A, K382A, R386A and K389A. In some aspects, the at least one substitution comprises R381D, K382A, R386D and K389A.

As used herein a non-LTR-retroelement reverse transcriptase refers to a RNA-dependent DNA polymerase encoded by a retrotransposon or by a free-standing gene lacking long terminal repeats or engineered versions thereof. Non-LTR-retroelement reverse transcriptases may comprise sequence dependent polymerase activity, sequence independent polymerase activity and template-switching activity. Non-LTR-retroelement reverse transcriptases have NTE, RT2a, and RT3a insertions and comprise a family of reverse transcriptases distinct from retroviral reverse transcriptases or LTR-containing-retroelement reverse transcriptase. Non-LTR-retroelement-reverse transcriptases are sometimes referred to as non-retroviral reverse transcriptases.

As used herein, "essentially free," in terms of a specified component, is used herein to mean that none of the specified component has been purposefully formulated into a composition and/or is present only as a contaminant or in trace amounts. The total amount of the specified component resulting from any unintended contamination of a composition is preferably below 0.01%. Most preferred is a composition in which no amount of the specified component can be detected with standard analytical methods.

As used herein in the specification and claims, "a" or "an" may mean one or more. As used herein in the specification and claims, when used in conjunction with the word "comprising", the words "a" or "an" may mean one or more than one. As used herein, in the specification and claim, "another" or "a further" may mean at least a second or more.

As used herein in the specification and claims, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating certain embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein. The patent or application file contains at least one drawing executed in color. Copies of this patent or patent application publication with color drawings(s) will be provided by the Office upon request and payment of the necessary fee.

FIGS. 2A-2E: Structural Overview and Comparison of GsI-IIC RT to HIV-1 RT and HCV RdRP. (A) Structure of GsI-IIC RT bound to RNA template (SEQ ID NO: 29)/DNA primer (SEQ ID NO: 28) and dATP substrate. α-helices and β-strands are labeled, and insert regions not present in retroviral RTs are demarcated with brackets. 'N' and 'C' denote N- and C-terminl of the protein. The RNA template and DNA primer sequences are indicated below. Fingers, salmon; insertions, red; palm, dark blue; thumb, green; D domain, yellow; RNA template, purple; DNA primer, cyan; dATP (stick representation; yellow). See also FIG. 8. (B) Schematic of protein-nucleic acid interactions. Bases, ribose rings, and phosphates are represented by rectangles, pentagons, and circles, respectively, and interactions between amino acids and nucleotides are indicated by a double black arrow (RNA 2' OH H-bond), black line (polar interaction), or dashed black line (non-polar interaction). Amino acid names are color-coded according to their domain location within the RT as in panel A. Nucleotide n−1 is the templating RNA base. (C-E) Comparison of GsI-IIC RT to HIV-1 RT (PDB:4PQU) and HCV RdRP (PDB:4WTA), aligned via the palm subdomain, two views with 90° rotation (helices in cylindrical cartoon, colors as above). For HIV-1 RT, RNase H and p51 regions are faded yellow and orange, respectively. For HCV RdRP, regions homologous to RT insert regions are labeled in quotation marks and non-homologous N- and C-terminal regions are faded silver and yellow, respectively.

Figure 9:
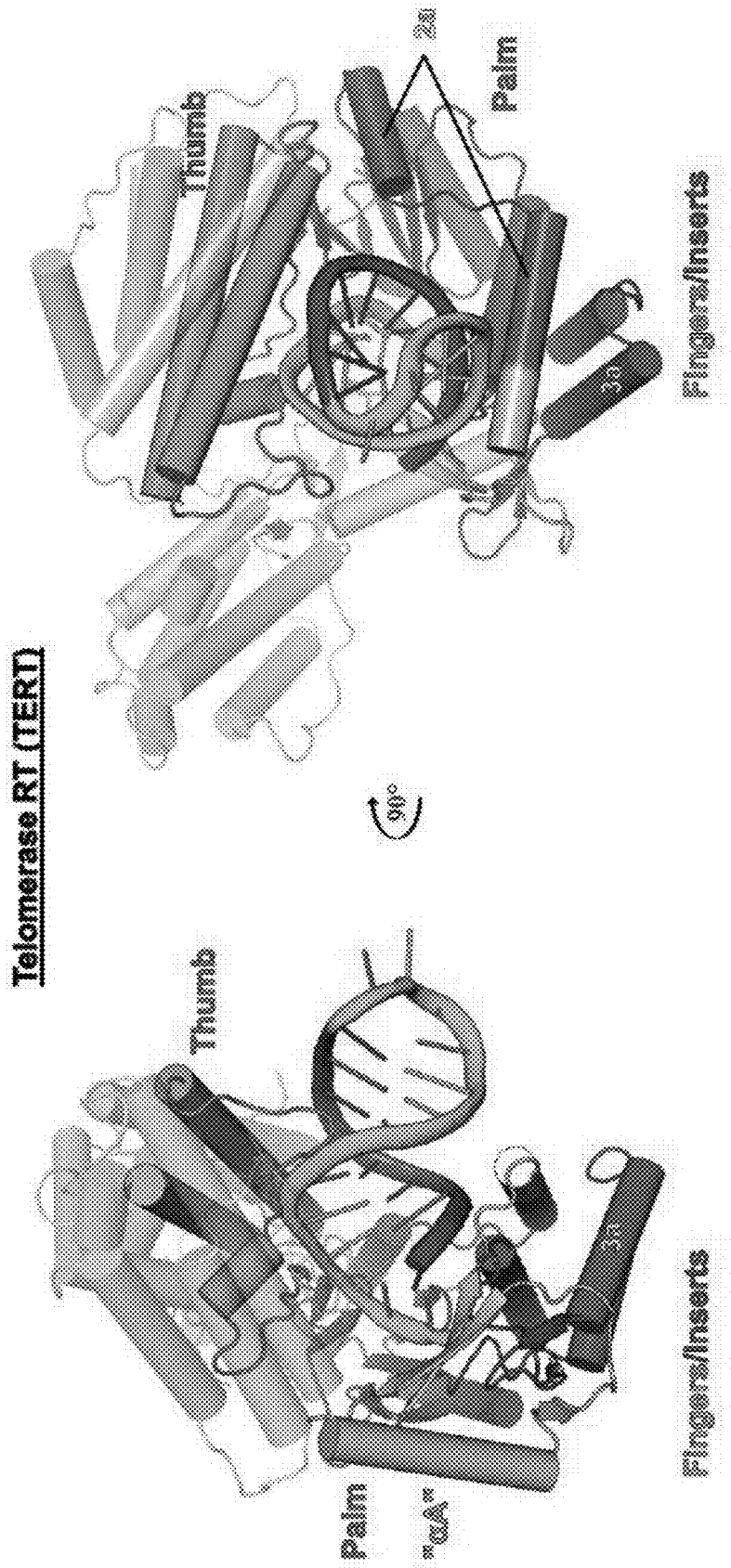

A similar depiction for telomerase RT is shown in FIG. 9. The orientation of GsI-IIC RT domains relative to the bound nucleic acid substrate more closely resembles HCV RdRP than HIV-1 RT.

FIGS. 3A-3I: Comparison of Active Site Regions of GsI-IIC RT, HIV-1 RT, and HCV RdRP. (A-C), (D-E), and (G-I) show three views highlighting different aspects for GsI-IIC RT, HIV-1 RT, and HCV RdRP, respectively. Regions are colored as in FIG. 2, and side chains important for catalytic pocket formation or function are labeled and shown in stick figure; catalytic $Mg^{2+}$ (green) or $Mn^{2+}$ (lime) are shown as spheres; the highly conserved YXDD and PQG motifs of the RT family and their homologs in RdRPs are circled with dashed lines. (A, D, G) dNTP-binding pocket showing the conformations of the YXDD/CGDD and PQG/ASG loops in the three polymerases. (B, E, H) Another view of the dNTP-binding pocket. The aromatic dNTP 'gating' residue below the nucleotide ribose moiety (F143 in GsI-IIC RT, Y115 in HIV-1 RT) is absent in HCV RdRP, but GsI-IIC RT and HCV RdRP possess a nearby conserved Asp (D144 or D225, respectively), which H-bonds (green dash) to the PQG or homologous ASG motif, potentially rigidifying the pocket. (C, F, I) Templating base (n−1)-binding pocket. While the HIV-1 RT templating base is held in place almost exclusively by weak hydrophobic interactions and is exposed in the major groove, in both GsI-IIC RT and HCV RdRP the RT0 motif forms a lid over n−1 in the major groove and H-bonds (green dashes) to the phosphates on either side of n−1.

FIGS. 4A-4I: Comparison of Template/Primer Binding between GsI-IIC RT, HIV-1 RT, and HCV RdRP. Three views for GsI-IIC RT, HIV-1 RT, and HCV RdRP are shown in panels A-C, D-F, and G-I, respectively. Nucleic acid and protein residues involved in binding the template/primer are depicted in stick figure; polar interactions are shown as green dashes; and the 'fingertips' β-hairpin loop is circled by a salmon dashed line (other colors as in FIG. 2). (A, D, G) Binding of the single-stranded 5' RNA overhang by GsI-IIC RT, HIV-1 RT, and HCV RdRP, respectively. GsI-IIC RT H-bonds to the phosphate backbone of every nucleotide from n−3 to n+1, while HIV-1 RT H-bonds only to the 2'-OH groups of nucleotide n−2 and n−1. The HCV-RdRP H-bonds to the n−1 and n+1 phosphates in a structure in which n−1 is the 5' terminal nucleotide (structures with longer 5' RNA overhangs unavailable). (B, E, H) Binding of the NTE in the major groove. Helix α1' of the NTE in GsI-IIC RT projects into the major groove of the nucleic acid duplex, making contacts to both template and primer in a region free of contacts in HIV-1 RT. The HCV RdRP "NTE" behaves similarly, with H95 and R109 being potential primer-binding homologs of Q24 and K18 in GsI-IIC RT (structures with longer HCV RdRP primers unavailable). See also FIG. 10. (C, F, I) Interaction of RT2a and neighboring regions with the RNA template. GsI-IIC RT forms 14 polar interactions (6 peptide-backbone H-bonds) with the RNA template, including 4 from RT2a (F110, R111, and N115 with 2' OHs; G113 with phosphate backbone).

HIV-1 RT makes only 6 polar contacts and one peptide backbone H-bond. HCV RdRP preserves the general shape of RT2a insert region but contacts primarily n−1 to n+3, leaving the remaining RNA nucleotides free of polar interactions (the crystallized HCV RdRP construct lacks a large C-terminal segment, which may make additional contacts to the RNA template).

FIGS. 5A-5C: Structure and Interactions of the GsI-IIC RT Thumb and D Domains with Template/Primer. (A, B) Comparison of thumb domain interactions with the DNA primer between GsI-IIC RT and HIV-1 RT, respectively. Y of the YXDD motifs (Y221 in GsI-IIC RT and Y183 in HIV-1 RT), the FLG/WMG motifs, the G-(X)3-Y/W motifs, nucleic acids, and dATP are labeled and shown in stick representation (colors as in FIG. 2). (C) Structure of the D domain and its interface with the thumb. Left, cartoon representation with potential nucleic acid-binding residues shown in stick figure, and a bound sulfate molecule shown as spheres (other colors as in FIG. 2). Right, electrostatic surface potential (red, negative; white, neutral; blue, positive). Electrostatic surface potential for the entire protein shown in FIG. 8C. Bottom: Amino acid sequence of the GsI-IIC RT thumb and a portion of the D domain (SEQ ID NO: 30), with bars representing α-helices. The residues with side chains displayed in (C) are highlighted in blue. See also FIG. 11.

FIGS. 6A-6D: RTO-Lid Mutations Inhibit Template-Switching Activity. (A) Model of the template-switching pocket. Space-filling format with semi-transparency around the RT0 loop and R85, colors as in FIG. 2. The bound template/primer substrate is depicted without n−2 to n+1 leaving a single-nucleotide 3' DNA overhang (p+1) in a pocket for binding of the 3' end of an incoming RNA template. (B) Electrostatic surface potential of the template-switching pocket, colors as in FIG. 5C. (C) and (D) Assays of template-switching and primer-extension activity, respectively. Reactions were carried out with unlabeled template RNAs and 5'-end labeled DNA primers in reaction medium containing 200 mM NaCl (optimal for template-switching) at 60° C. for times near the end of the linear range; cDNA products (arrows) were analyzed by denaturing PAGE. Lighter bands above the major template-switching product result from multiple end-to-end template-switches. Schematics of the reactions are shown beneath the gels, and the reactions are described in detail in Example 2.

FIGS. 7A-7D: Model of GsI-IIC RT Bound to a Group II Intron Lariat RNA and Adaptation of Group II Intron RT Regions for RNA Splicing. (A) Left, Model of GsI-IIC RT bound to a group IIC intron RNA lariat. The intron lariat (PDB:5J02) with the 5' end of the intron linked to the branch-point adenosine (5'I-BP, teal triangle) is poised to use its 3' OH (3'I-OH, orange circle) to attack the ssDNA exon junction (EJ). The latter is located downstream of a 5'-exon DNA hairpin recognized by the GsI-IIC RT. The black arrow denotes the gap (~6-Å, or 1 nucleic acid base) between 3' exon position +3 (from PDB:3IGI; 5' exon, 5' E; 3' exon, 3' E) and the 5' end of the RNA template strand in the crystal structure. The group IIC intron lariat RNA is depicted in faded space-filling format with DVI, cartoon white. GsI-IIC RT/template-primer complex is shown in cartoon cylinder format with regions colored as in FIG. 2 and template and primer 5' and 3' ends labeled. Right, Schematic of intron lariat RNA (gray) at a single-stranded DNA target site before (top) and after (bottom) reverse splicing into the DNA strand, labels as at left. (B) NTE/RT0 interactions. Left, GsI-IIC RT NTE/RT0 bound to template/primer structure with intron DVI positioned as in the model of panel A; middle, L1.LtrB RT NTE bound to DIVa(iii) from cryo-EM structure (PDB:5G2X); right, Prp8 NTE near the U2 branch-point recognition site bound to intron 3' end (U2-BP Recog. Site/3'I, PDB:5LJ3). (C) RT3a interactions. Left, GsI-IIC RT RT3a and 3a loop near PQG motif bound to template/primer; middle, L1.LtrB RT RT3a bound to intron DIVa(i) and (ii); right, Prp8 RT3a near U4 snRNA (PDB:SGAN) (D) Thumb and D domain interactions. Left, GsI-IIC RT thumb and D domain bound to template/primer with 5' exon (5' E, faded blue) model and IIC 5'-exon hairpin model (faded white) as in panel A; middle, L1.LtrB RT thumb and D domain bound to 5' exon and intron DI; right, Prp8 thumb and switch loop region bound to 5' exon and U5 snRNA 5'-exon recognition site (PDB:5LJ3).

FIGS. 8A-8C: Crystallographic Asymmetric Unit Details and Monomer Electrostatic Surface Potential. (A) Asymmetric unit contents of the GsI-IIC RT crystal structure showing the head-to-tail pseudo-symmetric dimer (fingers/inserts, red/pink shades; palm, blue shades; thumb, green shades; D domain, yellow shades; RNA template, purple shades; DNA primer, cyan shades). Boxes to the left and right show detailed views of the dimer interface (dashed regions). The right monomer, corresponding to chain A-C, was used for all depictions of GsI-IIC RT in the current work. (B) Overlay of the two monomers of the asymmetric unit aligned by the template/primer duplex, two views at 90° rotation. The tip of the D domain and exterior regions of the palm (dotted circles) displayed the most variability between monomers. (C) Two views at 180° rotation of the electrostatic surface potential of the right monomer.

FIG. 9: Structural Organization of Telomerase RT. Telomerase RT (PDB:3KYL), two views with 90° rotation, aligned along the palm subdomain as in FIG. 2C-2E (helices in cylindrical cartoon; fingers, salmon; conserved inserts, red; palm, blue; thumb, green; DNA nucleotides, cyan; RNA nucleotides, purple). The non-conserved N-terminal TRBD and C-terminal regions of the thumb are depicted in faded silver. The finger helix homologous to the HIV-1 RT helix αA is labeled.

Figure 10:
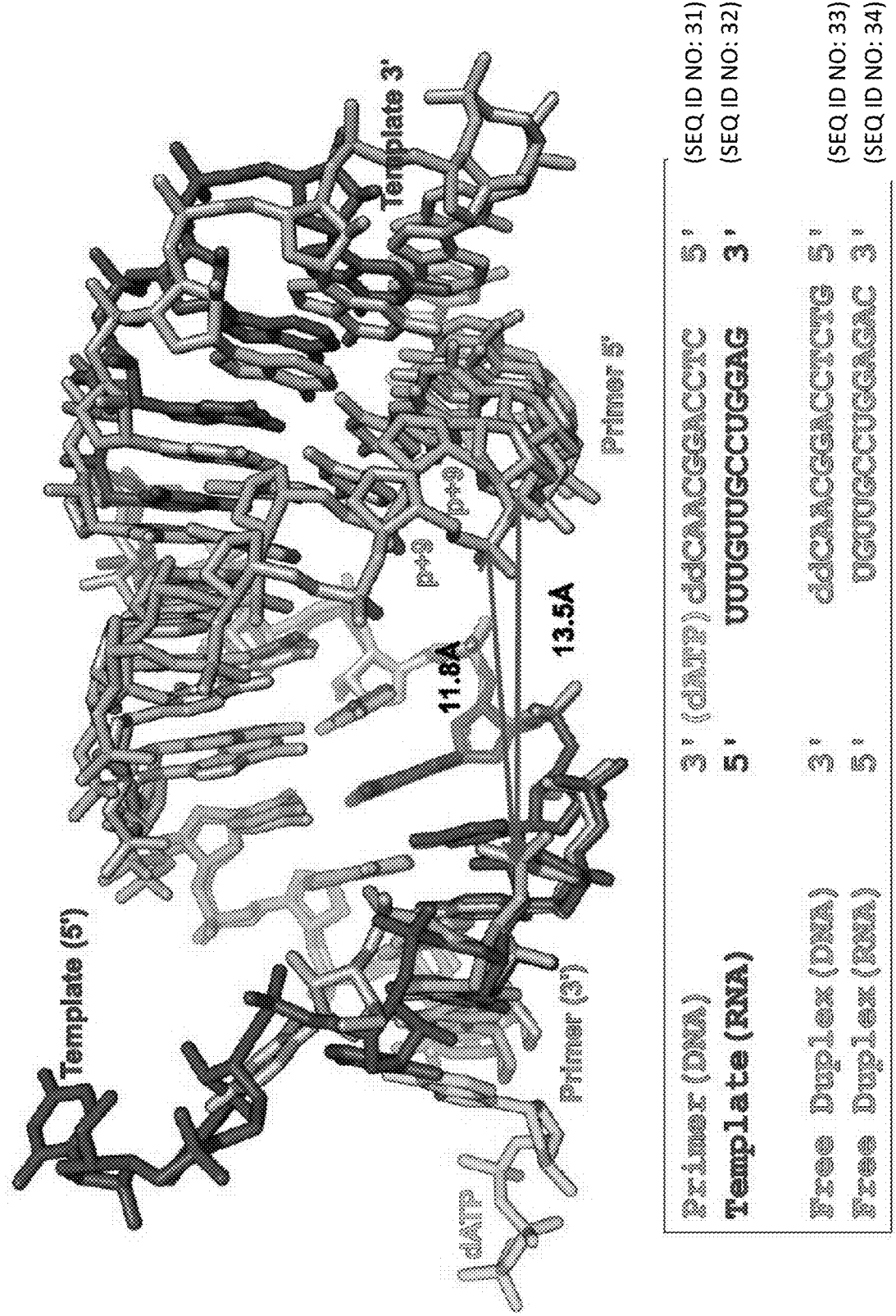

FIG. 10: Comparison of Bound versus Free Template/Primer Duplex. Comparison of the template/primer duplex found in the GsI-IIC RT complex to the crystal structure of a similar duplex (containing only one 5' overhang RNA base and two additional base pairs at the end of the duplex; PDB:6AR5), sequences and color-code shown below. The duplexes were aligned via the first 5 base pairs from the 5' RNA end, corresponding to RNA bases n+1 to n+5 and DNA bases p+1 to p+5. Red arrows indicate the distance from the n+2 phosphate to the p+9 phosphate (free duplex, 11.8A, protein-bound duplex, 13.5A).

Figure 11:
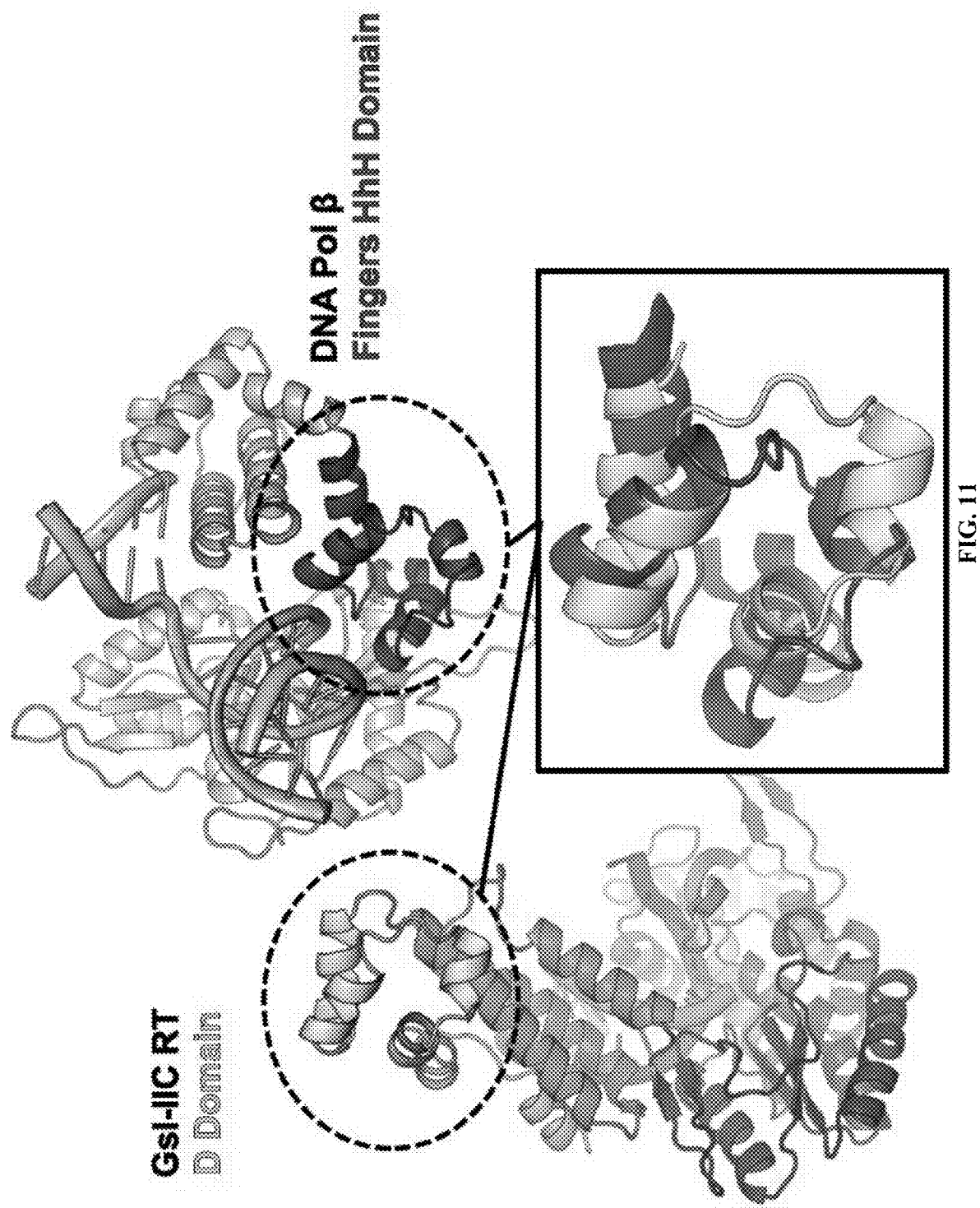

FIG. 11: GsI-IIC RT D Domain Similarity to a Helix-Hairpin-Helix DNA Binding Domain. Side-by-side comparison and overlay of the α-helical hairpin structures found in the GsI-IIC RT D domain (left, colored as in FIG. 2A) and the DNA polymerase β (PDB:1BPX) fingers helix-hairpin-helix (HhH) domain (right, silver with HhH domain in maroon). Structures within the dotted circle region are shown in close-up overlay, bottom right.

FIG. 12: GsI-IIC RT Amino Acid Coding Sequence. The GsI-IIC RT sequence (SEQ ID NO: 1) is shown with domains labeled.

Figure 13:
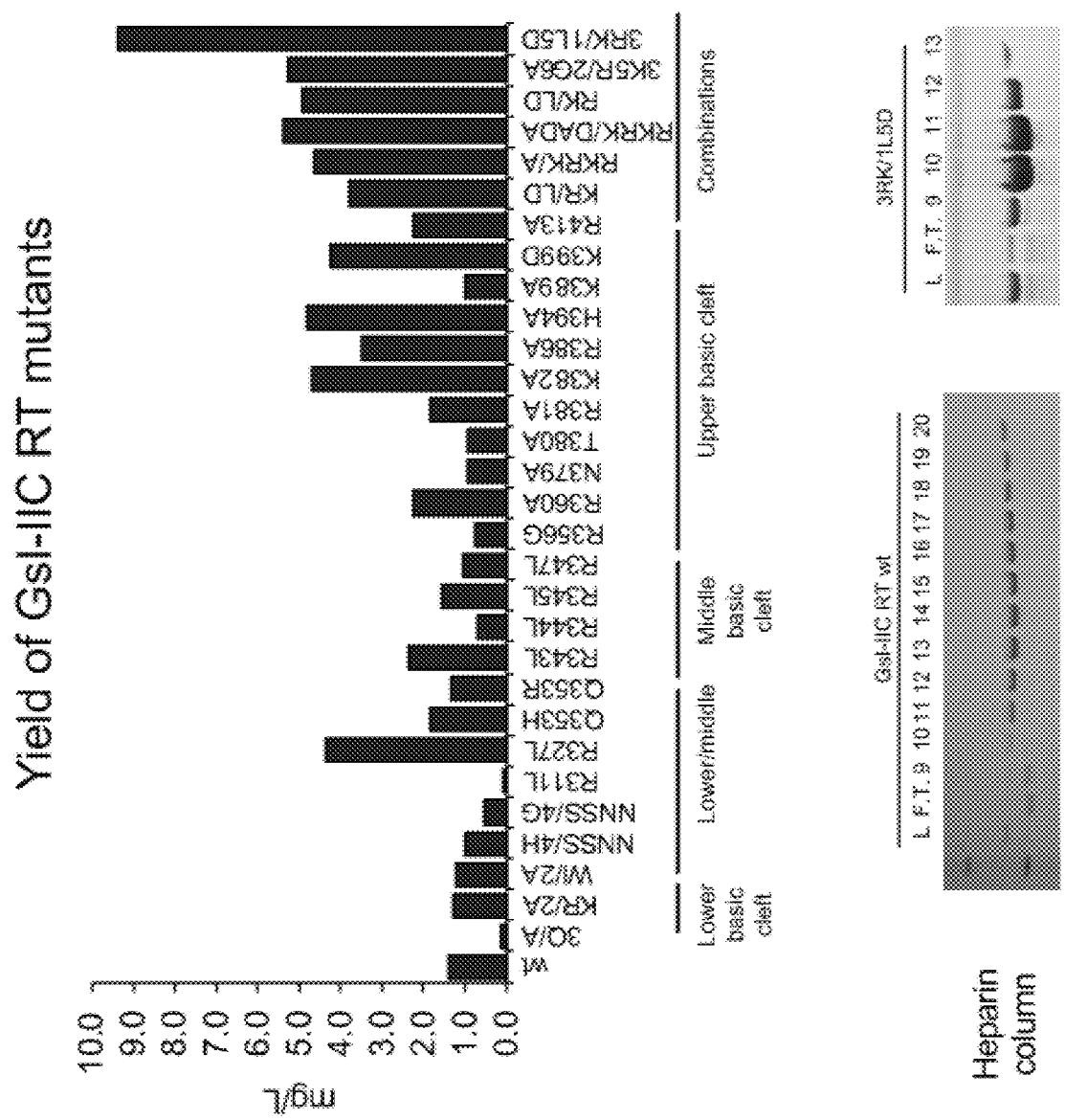

FIG. 13: Protein Production Yield with GsI-IIC RT Mutants. Additional amino acid substitutions were made on the surface of the GsI-IIC RT protein and the effects on protein production were tested. The top panel shows the yield of GsI-IIC RT mutant proteins. Proteins were purified as described in Biochemical Methods of the examples and protein concentration was measured by Bradford assay. The total yield was calculated per liter of culture medium. The y-axis indicates milligrams of protein per liter of LB culture medium. The x-axis lists the GsI-IIC RT mutants grouped by location. Combinations of single residue mutants (R343, R381, K382, R386, K389 and K399) gave higher yields than wild-type (WT) GsI-IIC RT. The 3RK/1L5D mutant showed the highest yield among all of the mutants tested in this experiment. Bottom panel: Coomassie stained SDS-polyacrylamide gel showing fractions from a heparin column for WT GsI-IIC RT and mutant 3RK/1L5D, respectively. See Table 3 for details on the mutations. The GsI-IIC protein in these experiments is fused at the N-terminus to a solubility tag (MalE protein) via a non-cleavable linker (Mohr et al., 2013).

Figure 14:
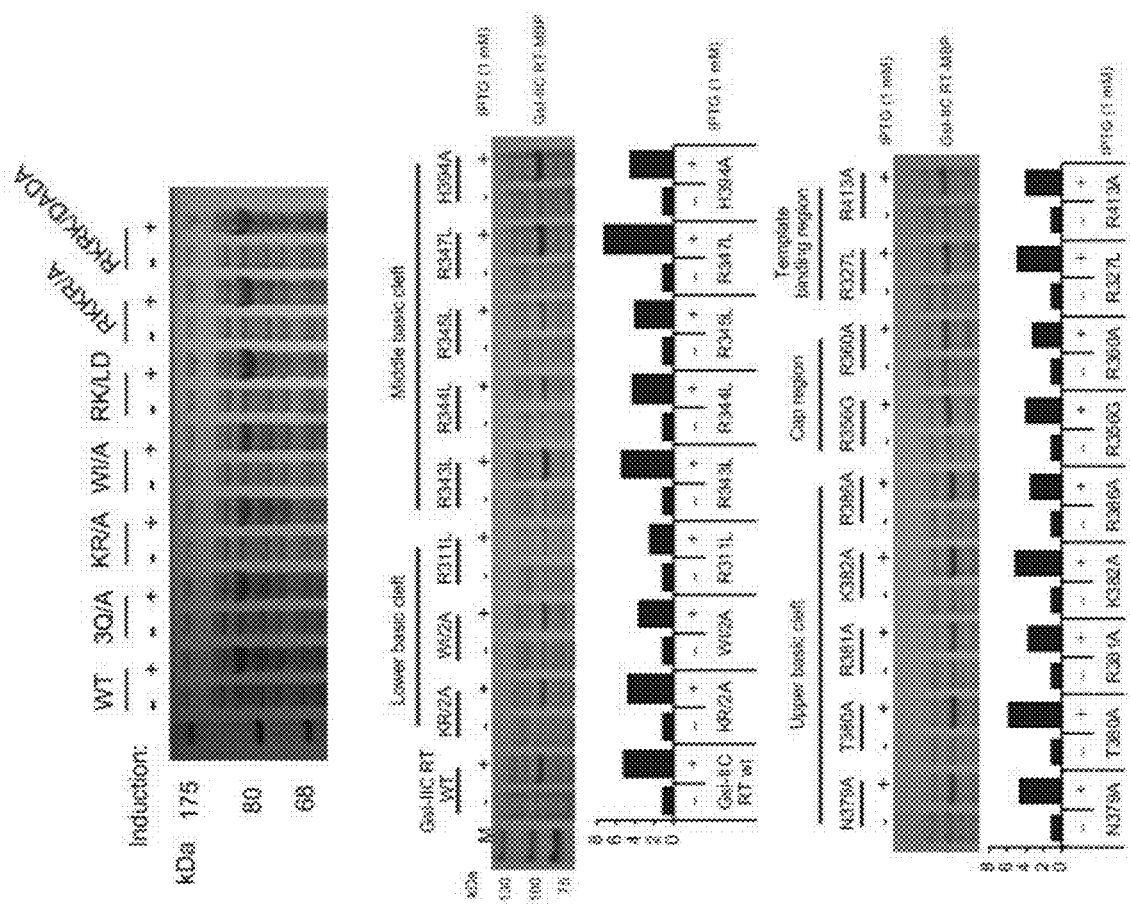

FIG. 14: Protein Production Yield with GsI-IIC RT Mutants. Verification of protein expression levels for single and double mutants of GsI-IIC RT by measuring soluble protein in cell lysates using Coomassie blue-stained SDS-polyacrylamide gels. Shown are cell lysates after induction with (+) or without (−) 1mM IPTG for 20 hours at 19° C. Cell pellets were resuspended and sonicated, as described in Biochemical Methods of Example 2—Methods and Materials. The same amount of supernatant was loaded on a SDS-PAGE gel. Mutants are grouped by location. All mutants expressed similarly when compared to WT GsI-IIC RT except for R311L. The size of protein markers are indicated on the left of each gel. See Table 3 for details on the mutations. The GsI-IIC protein in these experiments is fused at the N-terminus to a solubility tag (MalE protein) via a non-cleavable linker (Mohr et al., 2013).

Figure 15:
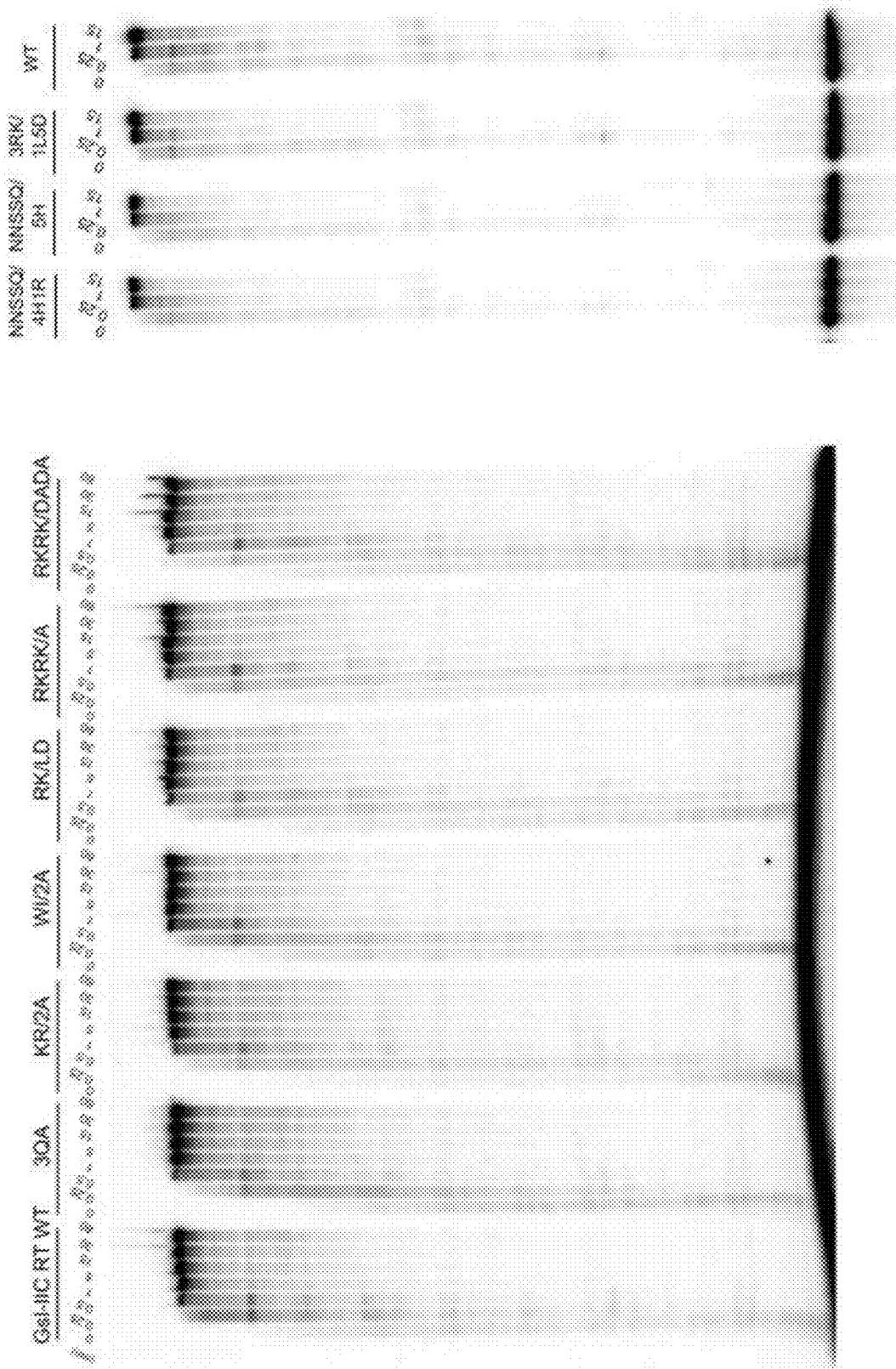

FIG. 15: RT Activity of GsI-IIC RT Mutants Having Multiple Substitutions. Primer extension assay time course experiments are shown for GsI-IIC RT mutants having multiple substitutions using a 1.1-kb in vitro transcribed RNA with an annealed DNA primer. Primer extension assays were conducted as described in Biochemical Methods of Example 2—Methods and Materials. All mutants showed comparable RT activity to WT GsI-IIC. See Table 3 for details on the mutations. The GsI-IIC protein in these experiments is fused at the N-terminus to a solubility tag (MalE protein) via a non-cleavable linker (Mohr et al., 2013).

FIGS. 16A-16D: RT Activity of GsI-IIC RT Mutants Having One or Two Substitutions. Primer extension assay time course experiments are shown for GsI-IIC RT mutants having one or two substitutions using a 1.1 kb in vitro transcribed RNA with an annealed DNA primer. Primer extension assays were conducted as described in Biochemical Methods of Example 2 Methods and Material. All mutants showed comparable RT activity to WT GsI-IIC RT. (A) Mutants in the lower basic cleft region; (B) Mutants in the middle basic cleft region; (C) Mutants in the Cap and RNA template region; (D) Mutants in the upper basic cleft region, see Table 3 for details on the mutations. The GsI-IIC protein in these experiments is fused at the N-terminus to a solubility tag (MalE protein) via a non-cleavable linker (Mohr et al., 2013).

Figure 17:
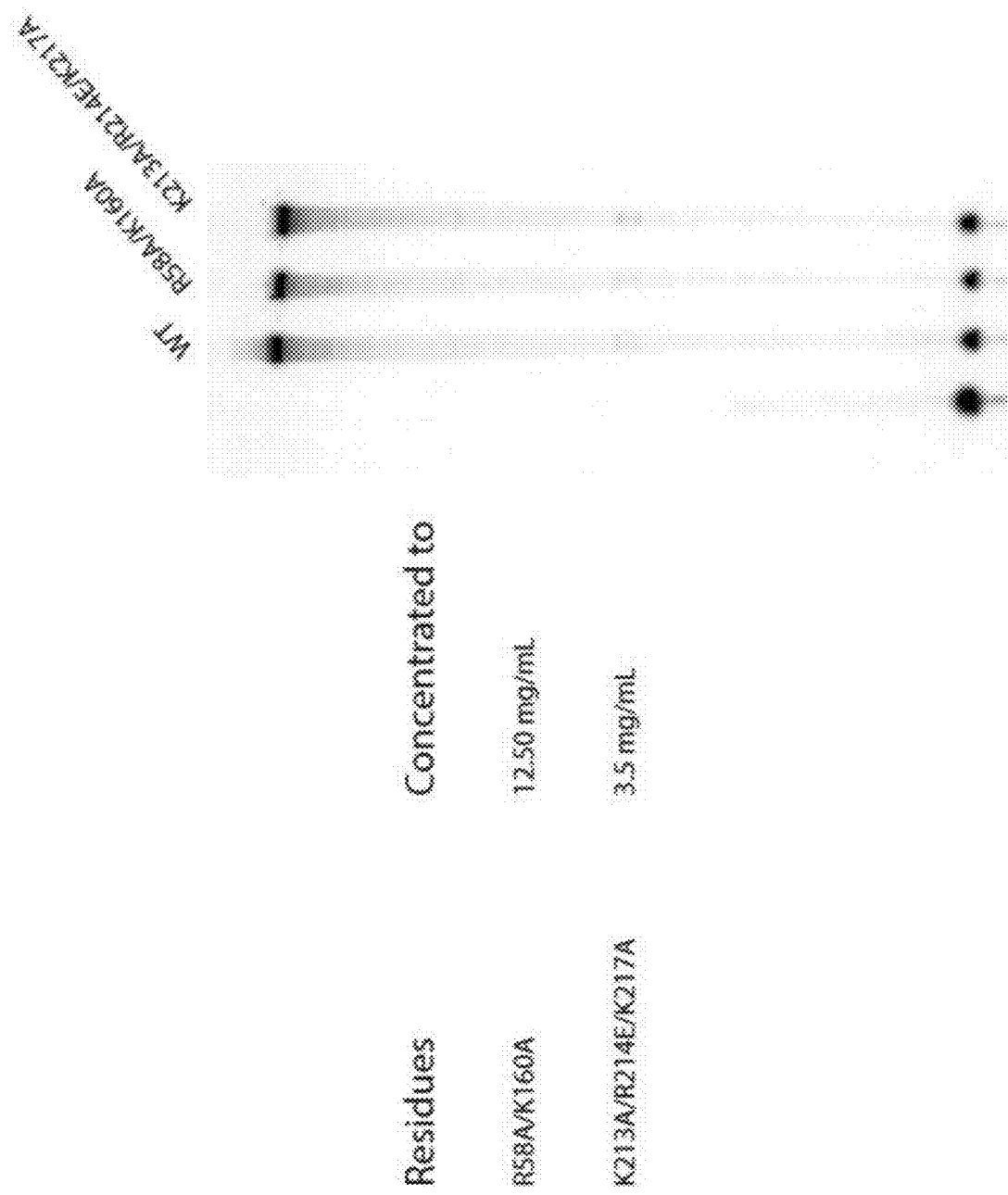

FIG. 17: RT Activity of GsI-IIC RT Fingers and Palm Domain Mutants. Some positively charged amino acid residues in the fingers and palm regions were mutated resulting in a R58A/K160A and K213A/R214E/K217A mutant. Mutants were concentrated using Amicon centrifugal filters to the indicated concentration (left). Primer extension reactions of wild-type, R58A/K160A, and K213A/R214E/K217A GsI-IIC RT using a 1.1 kb in vitro transcribed RNA with an annealed DNA primer (right). The reactions contained GsI-IIC RT (500 nM), 50 nM template-primer substrate, 200 mM NaCl and 1 mM of each dNTP and were incubated at 60° C. for 15 min. The products were analyzed by electrophoresis in a denaturing 6% polyacrylamide gel, which was dried and scanned with a PhosphorImager. See Table 3 for details on the mutations. The GsI-IIC protein in these experiments is fused at the N-terminus to a solubility tag (MalE protein) via a non-cleavable linker (Mohr et al., 2013).

DESCRIPTION OF ILLUSTRATIVE EMBODIMENTS

I. THE PRESENT EMBODIMENTS

Bacterial group II intron reverse transcriptases (RTs) function in both intron mobility and RNA splicing and are evolutionary predecessors of retrotransposon, telomerase, and retroviral RTs, as well as spliceosomal protein Prp8 in eukaryotes. The present studies determined a crystal structure of a full-length thermostable group II intron RT in complex with an RNA template/DNA primer and incoming dNTP at 3.0-Å resolution. It was found that the binding of template/primer and key aspects of the RT active site are surprisingly different from retroviral RTs, but remarkably similar to viral RNA-dependent RNA polymerases. The structure reveals a host of features not seen previously in RTs that may contribute to the distinctive biochemical properties of group II intron RTs, and it provides a prototype for many related bacterial and eukaryotic non-LTR-retroelement RTs. It also reveals how protein structural features used for reverse transcription evolved to promote the splicing of both group II and spliceosomal introns.

II. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Thermostable Group II Intron Reverse Transcriptase Characterization

Figure 1:
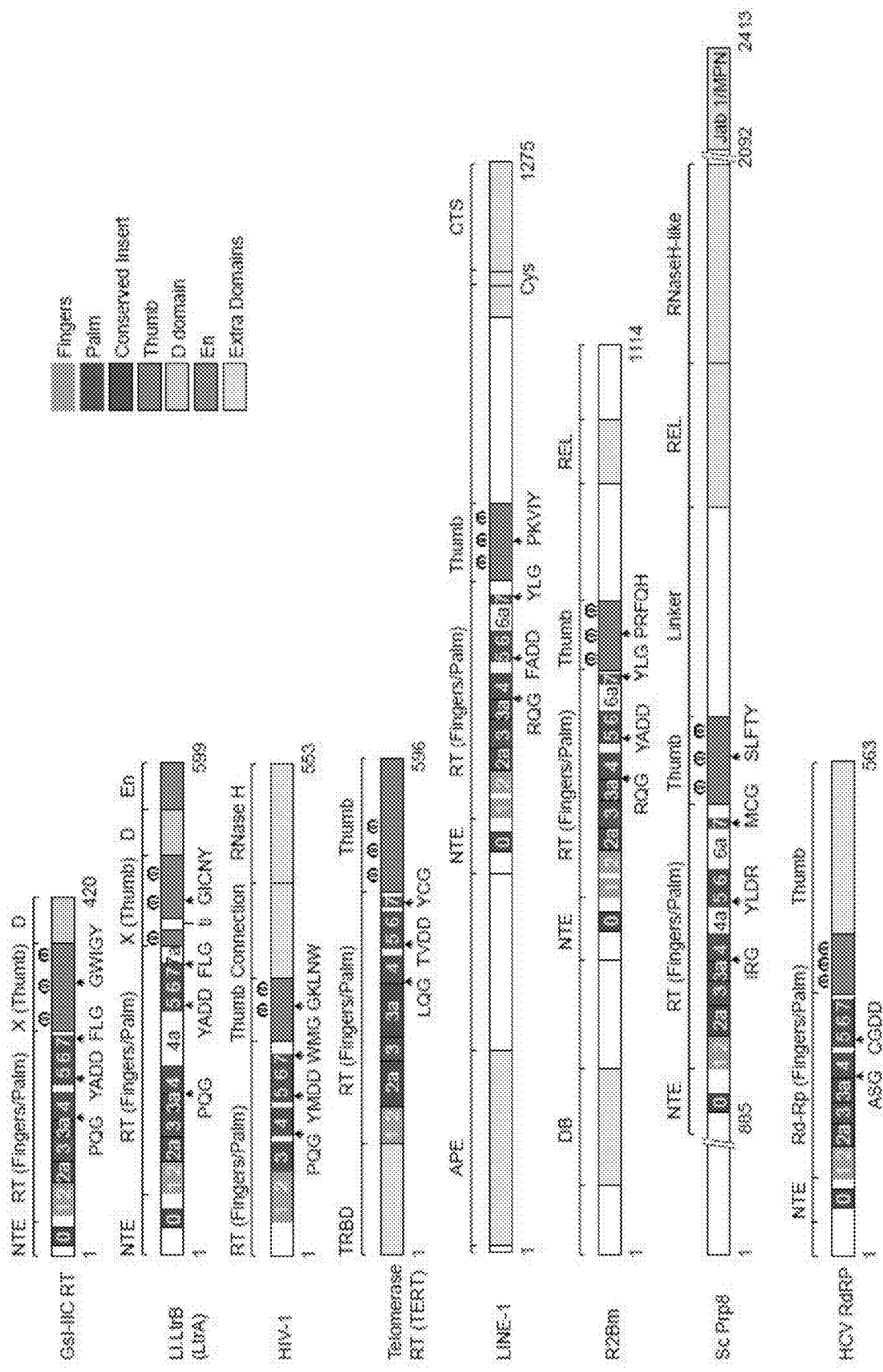
FIG. 1: Comparison of GsI-IIC RT to other RTs, Spliceosomal Protein Prp8, and HCV RdRP. The schematics show the domain organization and conserved sequences in *Geobacillus stearothermophilus* group IIC intron GsI-IIC RT (PDB:6AR1); group IIA intron L1.LtrB RT (LtrA protein; GenBank:AAB06503); retrovirus HIV-1 RT (PDB: 4PQU); *Tribolium castaneum* telomerase RT (PDB:3KYL); non-LTR-retrotransposon human LINE-1 RT (UniProtKB: 000370) and *Bombyx mori* R2Bm element RT (GenBank: AAB59214); *Saccharomyces cerevisiae* Prp8 (PDB:4I43); and hepatitis C virus (HCV) RdRP (PDB:4WTA). Conserved RT sequence blocks are numbered 0-7, and conserved sequence motifs are shown below each protein when present. APE, apurinic endonuclease domain; CTS, conserved carboxy-terminal segment; Cys, cysteine-rich conserved sequence; D or DB, DNA-binding domain; En, DNA endonuclease domain; REL, restriction endonuclease-like domain; TRBD, telomerase RNA-binding domain. (YADD=SEQ ID NO: 16; GWIGY=SEQ ID NO: 17; GICNY=SEQ ID NO: 18; YMDD=SEQ ID NO: 19; GKLNW=SEQ ID NO: 20; TVDD=SEQ ID NO: 21; FADD =SEQ ID NO: 22; PKVIY=SEQ ID NO: 23; PRFQH=SEQ ID NO: 24; YLDR=SEQ ID NO: 25; SLFTY=SEQ ID NO: 26; CGDD=SEQ ID NO: 27)

Comparison of Group II Intron RTs and Related Proteins: FIG. 1 compares the domain structures of two group II intron RTs, GsI-IIC RT analyzed in the present studies and the L1.LtrB RT (LtrA protein) studied previously, with a series of related proteins to which group II intron RTs were compared in this work. These include the retrovirus HIV-1 RT, telomerase RT (TERT), non-LTR-retrotransposon LINE-1 and R2Bm RTs, spliceosomal protein Prp8, and hepatitis C virus (HCV) RdRP. Like retroviral RTs, group II intron RTs have an N-terminal RT domain, which corresponds to the fingers and palm of the canonical right-hand like structure of nucleic acid polymerases and contains seven conserved sequence blocks (RT1-7) present in all RTs. Following the RT domain is a region corresponding to the thumb domain of retroviral RTs (Blocker et al., 2005). This region has been referred to as domain X and sometimes as the maturase domain because it was first identified as a site of mutations affecting the RNA splicing activity, but here we refer to it simply as the thumb. The RT (fingers/palm) domain of group II intron RTs is larger than those of retroviral RTs due to a distinctive N-terminal extension (NTE) with an additional conserved sequence motif RT0, and "inserts" between the conserved RT sequence blocks (e.g., RT2a, RT3a). The thumb domain of group II intron RTs is also larger than that of retroviral RTs, with three longer a-helices than retroviral RTs (Blocker et al., 2005). Notably, cognates of the NTE/RT0, RT2a, and RT3a and the longer thumb are also found in non-LTR-retrotransposon RTs, Prp8, and RdRPs (FIG. 1).

Appended to their common conserved RT and thumb domains, RTs and RdRPs have various additional N- and/or C-terminal domains that specialize the proteins for different functions. Group II intron RTs lack an RNase H domain present in retroviral RTs and instead have a C-terminal DNA binding domain (D), which contributes to recognition of the DNA target site for intron integration during retrohoming (San Filippo and Lambowitz, 2002). Most subgroup IIA and IIB intron RTs, including the L1.LtrB RT, have an additional DNA endonuclease (En) domain, which nicks the DNA target site to generate a primer for reverse transcription of the intron RNA, whereas group IIC introns, such as the GsI-IIC RT, lack an En domain and instead use a nascent strand at a DNA replication fork to prime reverse transcription (reviewed in (Lambowitz and Belfort, 2015)). Prp8 and some non-LTR retrotransposon RTs have a different appended DNA endonuclease domain (REL), which has not been found associated with a group II intron RTs, indicating multiple independent acquisitions of an En domain by this RT family.

Structure Determination and Overview: The full-length GsI-IIC RT (420 amino acids) with a C-terminal 8x histidine tag (i.e., 8 consecutive histidine residues added after amino acid position 420 of SEQ ID NO:1) was co-crystallized with an 11-bp RNA/DNA heteroduplex with a three nucleotide 5' overhang of the RNA template strand and a dideoxy nucleotide at the 3' end of the DNA primer in the presence of dATP and $Mg^{2+}$ to mimic an active polymerase conformation just prior to polymerization of an incoming dNTP (FIG. 2A). Nucleotide positions from the 5' to 3' end of the RNA template strand are denoted n−3 to n+11, with n−1 being the templating RNA base, and primer nucleotides are numbered p+1 to p+11 according to the base-paired nucleotide in the template. The complex crystallized in space group C2, and the structure was solved by a combination of multi-domain molecular replacement and seleno-methionine single-wavelength anomalous diffraction (SAD) phasing at 3.0-Å resolution (Table 1). The asymmetric unit contains two pseudosymmetric monomers (root mean square deviation (RMSD) of 0.88 Å) both bound to a template/primer in a head-to-tail dimer arrangement (FIG. 8A and 8B). All main chain atoms of GsI-IIC RT, except the N-terminal methionine and last two amino acids, are visible in the structure (FIG. 2A).

The GsI-IIC RT structure follows the canonical right-handed domain organization present in all other RTs of known structure, with 20 α-helices and 9 β-strands (FIG. 2A). As in other RTs, the fingers, palm, and thumb form a cleft, which binds the template/primer substrate, with the RT active site in the palm harboring the three highly conserved aspartates that bind two catalytic $Mg^{2+}$ ions. Notably, the distinctive group II intron RT insertions, NTE/RT0 (bent helices α1/α1' and α2/α2' separated by the conserved RT0 motif loop) and RT2a (α3 and α4) are seen to be integral parts of the fingers and palm that contribute to an extended binding interface with the nucleic acid duplex. By contrast, RT3a, which corresponds to the Insertion in Fingers Domain (IFD) in telomerase, forms an a-helical hairpin (α6 and α7) that packs into the interface of the fingers and palm domains on the side opposite the active site and does not contact the template/primer substrate (FIG. 2). The thumb domain inserts into the minor groove of the nucleic acid duplex, acting as a track for the elongating duplex as in HIV-1 RT, while the D domain forms a small globular capping structure at the top of the thumb with a helical tail that threads down along the outer face of the thumb to interact with the nucleic acid duplex, as described in more detail below.

Unlike HIV-1 RT, which functions as a heterodimer comprised of a catalytic p66 subunit and a structural p51 subunit, the group II intron RT binds the template/primer substrate as a monomer. The RT2a and RT3a inserts provide structural support for formation of the catalytic right-hand-like structure in the same manner as p51 in HIV-1 RT (FIG. 2C and 2D).

Surprisingly, the orientation of the fingers and thumb domain relative to the nucleic acid duplex differ markedly between GsI-IIC RT and HIV-1 RT (FIG. 2C and 2D). The change in orientation of the fingers reflects that the N-terminal (αA) helix of HIV-1 RT is positioned close to the 5' end of the template RNA overhang, while the NTE of GsI-IIC RT interacts extensively with the template/primer duplex at and downstream of the templating RNA base. The thumb of GsI-IIC RT is shifted upward toward the 5' end of the RNA template, with the distal regions of the thumb no longer contacting the duplex as in HIV-1 RT. As a result, GsI-IIC RT contacts only the first 7 bp of the template/primer duplex (positions +1 to +7; 1,551 $Å^2$ buried), whereas HIV-1 RT binds up to 19 bp of the duplex along an extended binding surface that continues from distal regions of the thumb along the connecting domain, parts of p51, and the RNase H domain (2,117 $Å^2$ buried; FIG. 2D). These extended contacts may reflect a requirement for RNase H cleavage of the copied RNA template strand by HIV-1 RT, whereas GsI-IIC RT lacks an RNase H domain and instead relies on a host RNase H to cleave the RNA template (Lambowitz and Belfort, 2015). Surprisingly, the configuration of the GsI-IIC RT fingers, palm, and thumb interacting with the template/primer substrate is remarkably similar to that of HCV RdRP (FIG. 2E), and it is shown below that the remarkable similarities extend to distinctive features of the RT active site and template/primer interactions.

RT Active Site: Overall, the structure of the GsI-IIC RT active site is similar to that of HIV-1 and other RTs, but with key differences that may enhance fidelity (FIG. 3). As in HIV-1 RT, the three catalytic aspartates (D138, D223, and D224) sit near the triphosphate of the incoming dNTP. D138 and D223 coordinate the dNTP-bound $Mg^{2+}$ ion. The second, lower affinity $Mg^{2+}$ is absent and D224 points away from the dNTP, as seen in an HIV-1 RT structure in the absence of a primer 3' OH with no impact on nearby residues except for the flipped orientation of the third aspartate (Lansdon, et al., 2010). Y221 points into the minor groove of the duplex, forming part of a pocket positioning the 3' end of the primer for polymerization. Surprisingly, in GsI-IIC RT, the highly conserved alanine of the YADD motif (A222, nearly invariant in group II intron RTs) is constrained by the presence of the similarly conserved, bulky F110 side chain, which protrudes into the active site from the RT2a insert. This feature has not been seen previously in any RT structure, but is similar to a G/F combination in the active site of HCV RdRP (G317/F193; FIG. 3G). The A222/F110 combination in GsI-IIC RTs replaces the conformationally more flexible M184 in HIV-1 RT and may contribute to a more restrictive binding pocket for the 3' end of the primer and correct base pairing of the incoming dNTP.

In the previous *Roseburia intestinalis* (R.i.) group II intron RT fragment structure, the RT3a insertion loop occupies the active site forcing the PQG motif near the beginning of RT4 into an inactive conformation (Zhao and Pyle, 2016). By contrast, in the GsI-IIC RT structure with bound template/primer, RT3a is flipped out of the active site, allowing the PQG loop to adopt an active conformation similar to that of HIV-1 RT (FIG. 3A and 3D, dashed circle). As in HIV-1 RT, the PQG loop helps position a conserved arginine (R75) of the 'fingertips' β-hairpin loop to pack against the ring of the incoming base, and both R75 and the nearby conserved lysine (K69) form canonical salt bridges to the triphosphate of the incoming dNTP.

As in all nucleic acid polymerases, the remainder of the dNTP-binding pocket in GsI-IIC RT is formed by the C-terminal end of a β strand (β5) and the following small helix (α5) of the palm (FIG. 3A and 3B). In both GsI-IIC RT and HCV RdRP, however, A114 at the beginning of the α5 cognate in HIV-1 RT is replaced by an aromatic (F142 and F224, respectively), which further constrains the dNTP-binding pocket (FIG. 3B, 3E, and 3H). Additionally, F116 toward the end of α5 in HIV-1 RT is replaced by a conserved acidic residue (D144 in GsI-IIC RT and D225 in HCV RdRP), which H-bonds to a residue in the PQG loop of GsI-IIC RT (Q191) or the structurally homologous ASG loop in HCV RdRP (S282) (FIG. 3B and 3H). These differences may stabilize the α5 helix, whose flexibility has been shown to affect the fidelity of RdRPs (Arnold et al., 2005).

Finally, GsI-IIC RT makes a series of novel contacts to the templating RNA nucleotide (n−1), which may deter misalignment of the template base. These include polar contacts to the phosphates on either side of n−1 from R85 of the fingers and the amide of A26 of RT0 and more extensive hydrophobic contact to the n−1 base by I79 (FIG. 3C and 3F). These interactions are not present in retroviral RTs, but mirrored in HCV RdRP by the n−1 base interactions of R168, A97, and Y162 (FIG. 3I).

Interactions of the GsI-IIC RT Fingers with the RNA Template Strand: In HIV-1 RT, contacts with the incoming RNA template strand are made by residues near αA, which is not present in GsI-IIC RT, and by the fingertips loop, which is present in GsI-IIC RT and interacts similarly with the bases of n−1 and n+1 through a series of hydrophobic residues (V65, I67, L77 in GsI-IIC RT or F61, I63, L74 in HIV-1 RT) (FIG. 4A and 4D). Additionally, the main-chain carboxyl group of the G of the PQG motif binds the 2' OH of the templating RNA base n−1 in both GsI-IIC RT and HIV-1 RT (G192 and G152, respectively). In HIV-1 RT, the mutation of F61 in the fingertips to leucine, a branched hydrophobic, increases strand-displacement activity (Fisher et al., 2003). Notably, the fingertips of GsI-IIC RT and other group II intron RTs contain two conserved branched hydrophobics (V65 and I79), a somewhat conserved P residue (P68), and a highly conserved basic residue (R63) that makes a unique contact to a kinked conformation of the n−2 phosphate backbone (FIG. 4A and 4D). These residues might contribute to the higher strand displacement activity of group II intron RTs by disrupting duplex-favorable orientations of the upstream bases.

Functions of the NTE/RT0 and RT2a Insertions: Strikingly, the GsI-IIC RT structure shows that the NTE/RT0 and RT2a insertions of group II intron RTs contribute extensive template/primer interactions around the RT active site, which are not present in retroviral RTs but comparable to those in viral RdRPs. For retroviral RTs, the major groove of the bound template/primer duplex is devoid of protein contacts and completely exposed to solvent (FIG. 4E). By contrast, the NTE of GsI-IIC RT inserts into the major groove of the template/primer duplex between positions +1 and +8 (FIG. 4B and 4E) with no major protein structural rearrangements compared to the unbound NTE in the R.i. RT fragment structure (0.82 Å RMSD over 48 residues; (Zhao and Pyle, 2016)). In the complex, Q24 at the tip of α1' and K18 on the second turn contact the primer DNA backbone phosphates of p+6 and p+8, while the conserved RT0 loop forms a 'lid' over the RNA template strand, a structure that has no cognate in retroviral RTs. Three residues of the NTE (R19 and N23 in α1' and the backbone amide of A26 in RT0) completely sandwich the backbone phosphates of the RNA template strand from n+1 to n+3 and most of the 5' phosphate of n−1. The conserved hydrophobic (I29) and D30 residues of RT0 (C-terminal to the 'lid' region) may help to anchor the loop in place, along with R85 (see below). Both the NTE protrusion into the major groove and the RT0 'lid' are similar in HCV RdRP (FIG. 4H).

The RT2a insertion of GsI-IIC RT consists of α3 and α4 joined by an extended loop (FIG. 4C). The latter contains F110, which protrudes toward the active site and packs against the alanine of the YADD motif (see above). The α3 helix of RT2a packs on the exterior of the fingers, while the α4 helix packs against the β5-β7 sheet of the palm domain. These features suggest that a major function of RT2a is to provide a supporting surface for the RNA template strand along the face of the RT where the duplex emerges after polymerization, a region partially supported by the p51 subunit of HIV-1 RT. Notably, while the HIV-1 RT duplex binding cleft between fingers and thumb contains only a few residues that H bond to the RNA template strand (E89 of p66 and K22 of p51), GsI-IIC RT makes a number of polar interactions to the substrate duplex, which are provided primarily by the RT2a insert (the backbone carbonyls of F110 and R111, the amide of G113, and the side chain of N115) and by nearby residues from the fingers and base of the thumb (FIG. 4C and 4F). In HCV RdRP, the RT2a homologous region spatially resembles that of GsI-IIC RT and closely approaches the RNA template, but makes fewer polar contacts with the RNA template strand (FIG. 4I). The higher number of RNA template/protein polar interactions from GsI-IIC RT RT2a may help compensate for the shortened duplex interacting surface compared to HIV-1 RT and could contribute to higher processivity.

Notably, the positioning of the first helix of the GsI-IIC RT NTE sterically precludes the RNA/DNA duplex in our structure from adopting the same conformation as RNA/DNA duplexes in HIV-1 and TERT (Das et al., 2014; Mitchell et al., 2010). Because of the location of the α1'helix of the NTE, the second turn of the duplex is displaced toward the thumb domain, resulting in a distortion of the duplex shape and a widening of the major groove. As a result, the distance between the n+2 and p+9 phosphates widens to 13.5 Å compared to 11.2 Å in the HIV-1 RT structure (PDB:4PQU, FIG. 4B and 4E). In the absence of the protein, the RNA/DNA duplex used in the GsI-IIC RT structure (with the addition of two base pairs on the duplex end) adopts a more compact A-form-like conformation as expected (FIG. 10), indicating that the distortion results from protein contacts.

Thumb Domain: The thumb domain of GsI-IIC RT adopts an elongated parallel three-helix structure similar to those seen in Prp8 structures and the first 3 helices of the thumb of RdRPs (Appleby et al., 2015; Galej et al., 2013). The second helix of the GsI-IIC RT thumb is homologous to the first thumb helix in retroviral RTs and similarly occupies the minor groove of the template/primer duplex. The prominent conserved motif of the thumb of group II intron RTs, G-x-x-x-Y/F-Y/F, serves the same function as the G-x-x-x-W motif in HIV-1 and other retroviral RTs, whereby the glycine allows close approach of the helix to the minor groove, and the conserved aromatic side chain at the fifth position of the motif (Y325 in the case of GsI-IIC RT) forms a pi-pi stacking interaction with the DNA primer and presumably disfavors polymerization of RNA bases by clashing with their 2'-OH group (FIG. 5A and 5B).

The conserved FLG loop in RT7 of group II intron RTs is located in the palm at the base of the thumb in the same general position as the WMG loop ("primer grip") of HIV-1-RT and forms a similar pocket for proper positioning of the primer during catalysis (FIG. 5A and 5B). The highly conserved presence of a phenylalanine in this loop (F269) instead of tryptophan (W229 in HIV-1 RT) is explained by its proximity to the second helix (α4) of the RT2a insert of group II intron RTs. The smaller F in the FLG primer grip loop allows RT2a to pack against the palm domain in GsI-IIC RT, taking the place of a portion of the p51 monomer in the HIV-1 RT dimer structure (FIG. 5A and 5B).

The first and third helices of the thumb provide a structural scaffold for the second helix and harbor a number of positively charged residues, which form a strong basic patch on the side of the thumb opposite the polymerizing duplex (FIG. 5C). Due to the rigid extended helical structure, the tip of the GsI-IIC RT thumb points away from the duplex, with no additional loops or helices that bend back to contact the duplex as in HIV-1 RT or TERT (see FIG. 2C, FIG. 9).

DNA-Binding Domain: The remainder of the GsI-IIC RT protein is composed of the C-terminal DNA binding (D) domain. This domain forms a small globular structure, which caps the tip of the thumb in a series of α-helix hairpin structures, reminiscent of short α-helical hairpin domains often observed in canonical DNA-binding domains (Sawaya et al., 1997)(FIG. 5C, FIG. 11). Although most of the D domain is positioned away from the nucleic acid duplex, a short C-terminal helix (α18), the most conserved secondary structural element within the diverse sequences of the DNA-binding region of group II intron RTs (San Filippo and Lambowitz, 2002), packs against the longer helices at the bottom of the thumb domain and contacts the RNA template strand via an H-bond between R413 and the 2'-OH of n+6 (FIG. 5C).

Notably, the packing of the D domain along the outer surface of the thumb forms a highly positively charged cleft on the face of the thumb opposite that which binds the template/primer duplex (FIG. 5C, and FIG. 8C). This basic cleft occupies the same region of the thumb that binds intron DI and the 5'-exon in the L1.LtrB RT or snRNAs and the 5'-exon in Prp8, indicating a role in RNA splicing and/or DNA target site recognition activity rather than RT activity. The poor conservation of the D domain outside of the substrate-binding C-terminal helix in group II intron family members may reflect its divergence to bind diverse DNA target site sequences or structures in different mobile group II introns (Lambowitz and Zimmerly, 2011).

RT0 Loop Mutations Affect Template-Switching Activity: The GsI-IIC RT structure will enable comprehensive structure-function analysis of group II intron RTs, as well as their engineering for biotechnological applications. It was noticed that the NTE/RT0 lid forms a large pocket that could contribute to the potent template-switching activity of group II intron RTs by capturing the 3' end of an incoming template strand (FIG. 6A and 6B). To test this hypothesis, we constructed mutants with amino acid changes in the glycine-rich RT0 loop and the adjacent α3 helix and compared their ability to initiate cDNA synthesis at the 3' end of a target RNA by template-switching (FIG. 6C) or conventionally from a DNA primer annealed to an RNA template (FIG. 6D). The artificial template-primer substrate used to initiate the template-switching reaction had a single-nucleotide 3' DNA overhang (a G residue), which can base pair the 3' C residue of the target RNA, mirroring a likely in vivo configuration in which template-switching follows addition of a single non-coded nucleotide to the 3' end of a completed cDNA (Mohr et al., 2013).

Strikingly, it was found that replacing the entire RT0 loop (positions 23-31) with four glycines (23-31/4G) strongly decreased template-switching activity, while leaving high primer extension activity. Further dissection of the loop showed that replacement of the first half with 6 glycines (23-28/6G) had only a minimal effect on template-switching activity, possibly reflecting that the RT0 lid binds the RNA template primarily via peptide backbone interactions.

By contrast, the mutations I29R, an anchoring residue at the end of the lid, and R85A, a residue that structurally stabilizes the conformation of the lid, strongly decreased template-switching activity. The I29R mutants retained high primer extension activity, while the R85A mutant had some decrease in primer extension activity, possibly reflecting that the hydrophobic side chain stem of R85 forms part of the active site cavity below the n−1 templating base. A D30A mutation in the second half of the loop had a relatively mild effect on template-switching activity. The severe loss of template-switching activity when mutating anchoring residues of the RT0 loop highlights the importance of the structural integrity of the lid for trapping incoming templates for polymerization.

Adaptation of Template/Primer-Binding Regions for RNA splicing: The crystal structure enabled modeling of the binding of the full-length GsI-IIC RT to a group IIC intron lariat RNA (Costa et al., 2016) by using positioning information from the cryo-EM structures of the L1.LtrB RT bound to a group IIA intron RNA and spliceosomal protein Prp8 bound to snRNAs. In order to mimic the configuration of the complex during reverse splicing of the intron lariat RNA into a DNA target site during retrohoming, a DNA strand containing the exon junction (EJ) and 5'-exon hairpin recognized by group IIC introns was added to the model based on the position of an RNA bound at the exon-binding site in a group IIC intron structure (PDB:3IGI) (FIG. 7A). Remarkably, it was found that the entire GsI-IIC RT structure with the template/primer bound in its catalytic cleft could be docked onto the group IIC intron structure in a position that maintains previously observed intron and/or snRNA interactions in the L1.LtrB or Prp8 structures with minimal steric hindrance. This was possible because the group II intron RT binds the intron RNA on its exterior surface, leaving the interior RT catalytic cleft free to bind the template/primer substrate.

Comparison of the GsI-IIC RT model with the L1.LtrB and Prp8 spliceosome cryo-EM structures showed that key regions of the group II intron RT involved in binding the template/primer are dually functional and use non-overlapping regions to bind template/primer and RNA splicing substrates (FIG. 7B-D). Thus, NTE/RT0 binds the template/primer by using only the compact surface at the end of α1' and the RT0 motif loop, leaving the unoccupied α2 in close proximity to DVI in the model (FIG. 7B). In the L1.LtrB structure, α2' of the NTE and the outer face of RT3a form an extended RNA-binding surface for DIVa, an intron-specificity element, which was deleted from the crystallized group IIC intron used in the GsI-IIC model (FIG. 7B and 7C, middle). In Prp8, which is not a functional RT, the tip of the NTE is in proximity to the branch-point recognition site of U2 snRNA, a cognate of DVI, while the outer surface of RT3a is in proximity to a DIV-like stem-loop region of U4 snRNA (FIG. 7B and 7C, right). Similarly in the GsI-IIC RT structure, all of the thumb contacts with the template/primer duplex are made by the second helix on the inner face of the helical bundle leaving the remainder of the thumb and adjoining D domain free for other contacts (FIG. 7D, left). In the L1.LtrB structure, the outer surface of the thumb helical bundle binds the 5'-exon nucleotides that are base-paired to the exon-binding sequences in intron DI (EBS1 and EBS2), as well as another region of DI using the ti insert at the end of the first thumb helix, a feature not present in group IIC introns (FIG. 7D, middle). In the Prp8 structure, the outer surface of the thumb helical bundle binds the 5' exon and U5 snRNA, a cognate of the EBS1 sequence, thereby helping position the 5' exon near the active site of U6 snRNA (FIG. 7D, right). Finally, the elongated GsI-IIC RT thumb/D domain interface forms a basic cleft on the outer surface, which could potentially bind the 5'-exon hairpin for DNA target site recognition (FIG. 7A and 7D, left).

Remarkably, the GsI-IIC RT model indicates that after reverse splicing of the intron RNA into a DNA strand, the RT active-site cleft is precisely positioned to initiate reverse transcription by using an incoming nascent DNA strand as primer at or just downstream of the 3' end of the intron sequence (FIG. 7A). This finding suggests how the reverse splicing and reverse transcription steps might be seamlessly coordinated during retrohoming.

Thus, the present studies solved the crystal structure of the full-length thermostable group IIC intron RT (GsI-IIC RT) in complex with an RNA template/DNA primer duplex and dATP, the first non-LTR-retroelement RT for which such a structure has been determined. In addition to providing a prototype for a large group of related but structurally uncharacterized Non-LTR-retroelement RTs, the structure reveals remarkably close structural and mechanistic similarities between group II intron RTs and viral RdRPs, provides insight into the structural basis for the distinctive enzymatic properties of group II intron RTs, and suggests how RT structural features that initially evolved to promote reverse transcription have been adapted to bind group II intron and spliceosomal RNAs for RNA splicing.

Example 2

Methods and Materials

Constructs: Full length His-tag GsI-IIC RT used for crystallization contained the native N-terminus and was constructed by adding a non-cleavable 8× His tag directly to the C-terminus by PCR from a GsI-IIC RT pMal fusion vector described previously (Mohr et al., 2013). The PCR product was ligated into the pET14b expression vector (Millipore) using NcoI and PstI restriction sites. The vector was transformed into BL21-CodonPlus (DE3)-RIPL chemically competent cells (Agilent) and plated onto LB plates containing 100 µg/mL ampicillin and 25 µg/mL chloramphenicol.

Wild-type and mutant GsI-IIC RT proteins used in biochemical assays were expressed as maltose-binding protein rigid fusions from pMRF-GsI-IIC (Mohr et al., 2013). GsI-IIC RT mutants were constructed in pMRF-GsI-IIC by site-directed mutagenesis using a Q5 Site Directed Mutagenesis Kit (New England Biolabs) with primers listed in Table S2. Constructs were transformed into Rosetta 2 (DE3) (EMD Millipore) chemically competent cells and plated onto LB plates containing 100 µg/mL ampicillin and 25 µg/mL chloramphenicol. All constructs were verified by sequencing.

Protein Expression, Purification, and Crystallization: For His-tag GsI-IIC RT protein expression, starter cultures were prepared by inoculating 25 mL of LB containing 100 µg/mL ampicillin and 25m/mL chloramphenicol with a single colony and grown at 37° C. shaking overnight. 20 mL of starter culture was added to 1 L of LB shaking culture containing 100 µm/mL ampicillin and grown at 37° C. to an $OD_{595}$ of 0.6-0.8. Cells were induced by the addition of 1 mM isopropyl β-D-thiogalactoside (IPTG) and incubated at 37° C. for a further 2.5 hr. Cell pellets were collected by centrifugation and stored at −80° C. prior to purification.

For seleno-methionine substituted His-tag GsI-IIC RT production, metabolic inhibition was used to incorporate seleno-methionine. After starter culture growth as described above, cells were collected by centrifugation and resuspended in 1 mL M9 minimal media and then inoculated into 1 L of M9 minimal media and grown to an $OD_{595}$ of 0.3 at 37° C. shaking incubation. Solid amino acid supplements were added at 100 mg L-lysine, 100 mg L-phenylalanine, 100 mg L-threonine, 50 mg L-isoleucine, 50 mg L-leucine, 50 mg L-valine, and 50 mg L-seleno-methionine. Cells were incubated with shaking for an additional 20 min and then induced with 1 mM IPTG for 2 hr at 37° C. followed by 14 hr at 18° C. Cell pellets were collected by centrifugation and stored at -80° C. prior to purification.

For protein purification, cells from 1 L of culture of either native or seleno-methionine substituted His-tag GsI-IIC RT were resuspended in 40 mL of cold Lysis Buffer, containing 20 mM Tris-HCl pH 8.5, 100 mM NaCl, 10% glycerol, 5 mM imidazole, 0.1% β-mercapto-ethanol (β-ME), 0.2 mM phenylmethylsulfonyl flouride (PMSF), and one EDTA-free Complete protease inhibitor cocktail tablet (Roche). Cells were lysed by sonication at 4° C. Lysate was clarified by centrifugation at 40,000×g for 1 hr at 4° C. Clarified lysate was combined with 10 mL bed volume of Ni-NTA Agarose beads (Invitrogen) and incubated by slow rotation at 4° C. for 2 hr. The beads were washed with 250 mL Wash Buffer, containing 20 mM Tris-HCl pH 8.5, 100 mM NaCl, 10% glycerol, 5 mM imidazole, and 0.1% β-ME, under gravity flow. The beads were further washed with 150 mL of Wash Buffer containing an additional 50 mM imidazole. GsI-IIC RT was eluted from the beads by adding 5×5 mL of Elution Buffer, containing 20 mM Tris-HCl pH 8.5, 100 mM NaCl, 10% glycerol, 0.1% β-ME, and 250 mM imidazole. Eluted fractions were analyzed by SDS-PAGE, and fractions containing GsI-IIC RT were pooled and applied to a 5 mL HiTrap Heparin HP column (GE Healthcare) pre-equilibrated in Heparin Buffer A, containing 20 mM Tris 8.5, 100 mM NaCl, 10% glycerol, and 0.1% β-ME, at a flow-rate of 1 mL/min. The column was washed with 5 column volumes (CVs) of Heparin Buffer A. A 10 CV gradient was applied from Heparin Buffer A to 50% of Heparin Buffer B, containing 20 mM Tris-HCl pH 8.5, 2 M NaCl, 10% glycerol, and 0.1% β-ME. A final 5 CVs of 100% Heparin Buffer B was applied. GsI-IIC RT typically eluted during the final step at a purity of >98% by SDS-PAGE. Fractions containing GsI-IIC RT were pooled and incubated in the presence of 65-70% saturating ammonium sulfate for 2-3 hr on ice, as the protein could not be successfully concentrated by other means. The precipitated protein was then pelleted by centrifugation at 40,000×g for 1 hr at 4° C., with utmost care taken during aspiration of the supernatant to remove as much ammonium sulfate solution as possible. The protein was then resuspended in Crystallization Buffer, consisting of 20 mM Tris-HCl pH 8.5, 500 mM NaCl, 10% glycerol, and 5 mM DTT, to a final concentration of 2-3 mg/mL.

Annealed RNA/DNA duplex for crystallization trials was produced by combining the single-stranded RNA and DNA oligonucleotides (Integrated DNA Technologies) at a 1:1 molar ratio, heating to 82° C. for 2 min, and then slowly cooling to room temperature. The annealed duplex was then combined with the concentrated GsI-IIC RT at a 1:1.2 protein:nucleic acid molar ratio in Crystallization Buffer also containing 2 mM $MgCl_2$ and 1 mM dATP and incubated on ice for 30 min. Crystals were grown by the hanging drop vapor diffusion method, with the drop containing 0.5 μL of GsI-IIC RT/duplex combined with 0.5 μL of a well solution containing 0.1 M Tris-HCl pH 7.5-8.5 and 1.2-1.4 M sodium citrate tribasic dihydrate. Crystals grew as thin plates over the course of 1 to 2 weeks with dimensions of approximately 20 μm×50 μm×100 μm for seleno-methionine protein or 25 μm×100 μm×200 μm for native protein.

The RNA/DNA duplex-only crystals were obtained from hanging drop vapor diffusion experiments performed with a GsI-IIC RT/nucleic acid duplex complex prepared as described above, using a well solution containing 1.2 M sodium malonate pH 7.0 and 0.6 M ammonium citrate tribasic pH 7.0. Crystals grew to a 125 μm radius in 2-3 weeks.

Crystals were harvested with a cryoloop (Hampton Research), and immersed briefly in Al's oil (Hampton Research) for the GsI-IIC RT containing crystals, or paraffin oil for the duplex-only crystals, before flash freezing into liquid nitrogen.

Data Collection, Analysis, and Structure Determination: Diffraction data were collected at 100K at the Advanced Light Source (ALS) on beamline 5.0.3. Images were integrated using the XDS package (Kabsch, 2010) and scaled with Aimless (Evans and Murshudov, 2013). For the GsI-IIC RT/duplex complex, the initial molecular replacement model was obtained using the program EPMR (Kissinger et al., 1999). Initial refinement was carried out in the Phenix package (Adams et al., 2010), with subsequent refinement also incorporating Buster (Bricogne et al., 2016) and Refmac5 (Murshudov et al., 2011). Data collection and refinement parameters are reported in Table 1.

TABLE 1

Crystallographic Data Collection and Refinement Statistics, Related to Methods.

| | RT/Duplex (Nat) | RT/Duplex (Se-SAD) | Duplex only |
|---|---|---|---|
| Data Collection | | | |
| PDB ID | 6AR1 | 6AR3 | 6AR5 |
| Wavelength | 0.9765 | 0.9765 | 0.9765 |
| Resolution range | 47.5-3.0 (3.1-3.0) | 48.7-3.4 (3.5-3.4) | 36.1-2.4 (2.5-2.4) |
| Space group | C 1 2 1 | C 1 2 1 | P 31 2 1 |
| Unit cell: a, b, c (Å) | 179.2, 95.1, 71.6 | 179.5, 109.0, 72.5 | 46.4, 46.4, 82.2 |
| Unit cell: α, β, γ (°) | 90, 113.5, 90 | 90, 113.8, 90 | 90, 90, 120 |
| Total reflections | 166553 (16758) | 132407 (13028) | 88600 (8691) |
| Unique reflections | 21940 (2211) | 17492 (1724) | 4250 (407) |
| Multiplicity | 7.6 (7.6) | 7.6 (7.6) | 20.8 (21.4) |
| Completeness (%) | 99.8 (98.9) | 99.9 (99.7) | 99.9 (100.0) |
| Mean I/sigma(I) | 16.9 (2.0) | 9.1 (2.0) | 49.8 (6.6) |
| Wilson B-factor | 78.8 | 84.9 | 46.3 |
| R-merge | 0.112 (0.958) | 0.218 (1.01) | 0.0531 (0.557) |
| R-meas | 0.120 (1.03) | 0.234 (1.08) | 0.0545 (0.570) |
| R-pim | 0.0434 (0.371) | 0.0848 (0.393) | 0.0119 (0.123) |
| CC½ | 0.999 (0.874) | 0.996 (0.855) | 1 (0.977) |
| CC* | 1 (0.966) | 0.999 (0.96) | 1 (0.994) |
| Refinement | | | |
| Reflections used in refinement | 21940 (2211) | 17492 (1724) | 4249 (407) |
| Reflections used for R-free | 1092 (105) | 1736 (169) | 212 (15) |
| R-work | 0.216 | 0.273 | 0.185 |
| R-free | 0.255 | 0.324 | 0.212 |
| CC(work) | 0.884 | 0.781 | 0.967 |
| CC(free) | 0.934 | 0.703 | 0.986 |
| Number of non-hydrogen atoms | 7873 | 7660 | 577 |
| macromolecules | 7801 | 7598 | 556 |
| ligands | 72 | 62 | — |
| solvent | — | — | 21 |
| Protein residues | 832 | 837 | 0 |
| RMS(bonds) | 0.007 | 0.008 | 0.007 |
| RMS(angles) | 1.16 | 1.24 | 0.95 |
| Ramachandran favored (%) | 97.1 | 96.3 | — |
| Ramachandran allowed (%) | 2.7 | 3.5 | — |
| Ramachandran outliers (%) | 0.2 | 0.2 | — |
| Rotamer outliers (%) | 1.1 | 0.9 | — |
| Clashscore | 2.0 | 5.0 | 1.2 |
| Average B-factor | 87.3 | 99.5 | 39.8 |
| macromolecules | 87.3 | 99.6 | 39.9 |
| ligands | 81.7 | 87.2 | — |
| solvent | — | — | 38.7 |
| Number of TLS groups | 10 | — | — |

Statistics for the highest-resolution shell are shown in parentheses.

The protein/nucleic acid complex crystallized in space group C2, and the structure was solved by a combination of multi-domain molecular replacement and seleno-methionine single-wavelength anomalous diffraction (SAD) phasing. The data display anisotropy, with $CC_{1/2}$=0.5 to 2.6 Å in the h direction, but only to 3.4 Å in the k direction (with the 1 direction intermediate). Including higher resolution data did not enhance the electron density; therefore, 3.0 Å resolution was chosen according to the criterion of the mean I/sigma (I)=2.0 in the highest resolution shell. A combination of the molecular replacement solution obtained in EPMR using the R.i. fingers/palm domain (PDB:5IRF) and the TERT RNA/DNA hairpin (PDB: 3KYL) with Se-Met SAD phases using the MR-SAD feature from the Phenix package in the GsI-IIC RT/Duplex (Se-SAD) dataset (a=179.5, b=109.0, c=72.5Å, β=113.8° ; PDB:6AR3) yielded initial density for the missing thumb and D domain, with the seleno-methionine locations matching with expected positioning based on homology to known RT structures. However, refinement stalled at high R-factors (~40% $R_{free}$), with many side chains absent and much of the thumb and D domain backbone trace unclear. After the crystals had remained in the drop for several months, C2 crystals with a slightly compacted unit cell were obtained (GsI-IIC RT/Duplex (Nat); PDB:6AR1)(a=179.2, b=95.1, c=71.6Å, β=113.8°; PDB:6AR3). Molecular replacement followed by rigid body refinement was carried out using the model from the GsI-IIC RT/duplex (Se-SAD) data set, with more difference density features apparent. Once most of the model had been built (bulk solvent parameters, NCS restraints, TLS, and individual temperature factors applied during refinement), rigid body twin refinement (twin law h+2*1, -k, -l, twin fraction=0.5) with the fingers, palm, thumb, and duplex domains as independent bodies (carried out in Refmac5) revealed the different domain conformations amongst the two monomers in the asymmetric unit and allowed completion of the refinement. Note that the pseudo-merohedral twin law combined with the pseudo-symmetry of the two molecules in the C2 asymmetric unit cause the data to assume an apparent $I222/I2_12_12_1$ symmetry. The structure may also be partially solved and refined in the I222 space group, but with similar poor density and stalled R-factors as described above. The $R_{free}$ set was chosen to match both pseudo-symmetry related and twin related reflections. Model building was performed in Coot (Emsley et al., 2010). The monomer composed of chains A, B, and C were used throughout this work for depictions and structure analysis due to having more visible density for the loop region between helices α10 and α11 and the non-protein-bound end of the nucleic acid duplex.

The nucleic acid duplex-only crystallized in space group $P3_121$ with unit cell constants as in Table 1 (PDB:6AR5). The structure was solved by molecular replacement in Phaser using the isolated RNA/DNA duplex chains from the native data set. Refinement was carried out in Phenix and model building in Coot, applying bulk solvent parameters and individual temperature factors.

Biochemical Methods: Wild-type and mutant GsI-IIC RT proteins were expressed from pMRF-GsI-IIC (see above) with maltose-binding protein fused to their N-termini via a non-cleavable rigid linker with minor modifications of the previously described procedure (Mohr et. al., 2013). Briefly, transformed single colonies of Rosetta 2 (DE3) cells (EMD Millipore) were inoculated into 100 mL LB+ampicillin/chloramphenicol media and grown overnight with shaking at 37° C. The starter culture was added to 1 L of LB+ampicillin media (ratio of 1:50) and grown at 37° C. to an $OD_{600}$ of 0.6-0.7. Protein expression was induced by adding 1 mM IPTG and incubating at 37° C. for 2 hr. Cells were pelleted by centrifugation and stored in −80° C. overnight. Cells were thawed and then lysed by sonication in 20 mM Tris-HCl pH 7.5, 500 mM KCl, 20% glycerol, 1 mg/mL lysozyme, 0.2 μM. The lysate was clarified by centrifugation at 24000 ×g for 1 hr at 4° C. Polyethyleneirnine (PEI) was added slowly to the clarified lysate to a final concentration of 0.4% in order to precipitate nucleic acids and centrifuged at 24000×g for 25 min at 4° C. Nucleic-acid free GsI-HC RT was precipitated from the supernatant with 60% saturating ammonium sulfate, and resuspended in A1 buffer (25 mM Tris-HCl pH 7.5, 300 mM KCl, 10% glycerol). The protein was then loaded onto MBPTrap HP column (GE Healthcare), washed with 10 CVs of A1 buffer, 6 CVs of A2. buffer (25 mM Tris pH 7.5, 1.5 M KCl, 10% glycerol), and again with 6 CVs of A1 buffer. GsI-IIC RT was eluted with 10 CVs of 25 mM Tris-HCl pH 7.5. 500 mM KCl., 10% glycerol containing 10 mM maltose. Fractions containing protein were diluted to 100 mM KCl, loaded onto a HiTrap Heparin HP column (GE Healthcare), and eluted with a 12 CV gradient from buffer A1 to A2. Fractions containing GsI-IIC RT were identified by SDS-PAGE, pooled, and dialyzed into 20 mM Tris-HCl pH 7.5, 500 mM KCl, 50% glycerol. RT aliquots were flash frozen using :liquid nitrogen and stored in −80° C.

Template-switching and primer extension assays were carried out using GsI-IIC-MRF RT, as described (Mohr et al., 2013). The initial template-primer substrate used for template switching reactions was the same as that used for RNA-seq adapter addition in RNA-seq protocols (Nottingham et al., 2016). It consists of a 34-nt RNA oligonucleotide containing an Illumina R2 sequence (R2 RNA; Table 2) with a 3'-blocking group (3SpC3; Integrated DNA Technologies) annealed to a 35-nt 5'$^{32}$P-labeled DNA primer ([γ-$P^{32}$]-ATP, Perkin Elmer), which contains the reverse complement of the R2 sequence and leaves a single nucleotide 3' G overhang (R2RG DNA; Table 2). The oligonucleotides were annealed at a ratio of 1:1.2 to a yield a final duplex concentration of 250 nM by heating to 82° C. for 2 min and then slowly cooling to room temperature. GsI-IIC RT (400 nM) was preincubated with the annealed R2/R2R-G heteroduplex (50 nM) and 50-nt acceptor template RNA (100 nM) in final 10 μl of reaction medium containing 200 mM NaCl, 5 mM $MgCl_2$, 20 mM Tris-HCl pH 7.5, and 5 mM DTT for 30 min at room temperature, and the template-switching reverse transcription reactions were initiated by adding 0.4 μL of 25 mM dNTPs (an equimolar mix of 25 mM dATP, dCTP, dGTP, and dTTP, Promega). Reactions were incubated at 60° C. for 15 min and stopped by adding 5 μL of the reaction mixture to 15 μL of 0.25 M EDTA. The RNA templates were then degraded by adding 1 μL of 5 N NaOH and heating to 95° C. for 3 min followed by a cooling to room temperature and neutralization with 1 μL of 5 N HCl. 10 μL of formamide loading dye (95% formamide, 0.025% xylene cyanol, 0.025% bromophenol blue, 6.25 mM EDTA) was added and products were denatured by heating to 99° C. for 10 min and placed on ice prior to electrophoresis in a denaturing 8% TBE-Urea polyacrylamide gel. The gel was dried, exposed to a phosphor screen, and scanned using a Typhoon phosphorimager at a PMT of 1000.

TABLE 2

Biochemical Assay and Site-directed Mutagenesis Oligonucleotides, Related to Methods.

| Primers | Sequence |
|---|---|
| *Biochemical Assays* | |
| AML1 | TCTTCGGGGCGAAAACTCTCAAGGATCTTACCG CTGTTGAGATCCAGTTC (SEQ ID NO: 2) |
| R2RG | GTGACTGGAGTTCAGACGTGTGCTCTTCCGATC TG (SEQ ID NO: 3) |
| R2 | rArGrArUrCrGrGrArArGrArGrCrArCrAr CrGrUrCrUrGrArArCrUrCrCrArGrUrCrA rC/3SpC3/ (SEQ ID NO: 4) |
| Acceptor RNA oligo | rCrGrCrCrGrGrArCrCrGrUrGrCrArCrCr ArUrCrUrGrGrArGrUrUrArUrArGrArGrA rUrGrArGrUrCrUCrArCrArUrArGrArCrC (SEQ ID NO: 5) |
| *Site-directed Mutagenesis* | |
| 23-28 F' | GGCGGCGGCATCGACGGAGTATCAACCG (SEQ ID NO: 6) |
| 23-28 R' | GCCGCCGCCGGCTTCGACCCGTTTGAG (SEQ ID NO: 7) |
| 23-31 F' | GGCGGCGTATCAACCGATCAACTCCG (SEQ ID NO: 8) |
| 23-31 R' | GCCGCCGGCTTCGACCCGTTTGAG (SEQ ID NO: 9) |
| I29R F' | AGCACCGGGACGAGACGGAGTATCAACC (SEQ ID NO: 10) |
| I29R R' | CCTTGGTTGGCTTCGACC (SEQ ID NO: 11) |
| D30A F' | ACCGGGAATCGCTGGAGTATCAACC (SEQ ID NO: 12) |
| D30A R' | GCTCCTTGGTTGGCTTCG (SEQ ID NO: 13) |
| R85A F' | CGTGGTGGACGCACTGATCCAACAAGC (SEQ ID NO: 14) |
| R85A R' | GTGGGAATGCCTAGCTGC (SEQ ID NO: 15) |

Primer extension reactions were carried out similarly using a 50-nt 5'$^{32}$P end-labeled DNA primer (AML1; Table 2) annealed near the 3' end of a 1.1 kb in vitro transcribed RNA. The transcript was generated by T3 runoff transcription (T3 MEGAscript kit, Thermo Fisher Scientific) of pBluescript KS (+) (Agilent) linearized using XmnI (New England Biolabs) and cleaned up using a MEGAclear kit (Thermo Fisher Scientific). The labeled DNA primer was annealed to the RNA template at a ratio of 1:1.2 to a yield a final duplex concentration of 250 nM by heating to 82° C. for 2 min followed by slowly cooling to room temperature. GsI-IIC RT (400 nM) was preincubated with 50 nM of the annealed template/primer in final 10 µl of reaction medium containing 200 mM NaCl, 5 mM MgCl$_2$, 20 mM Tris-HCl pH 7.5, 5 mM DTT for 30 min at room temperature, and reverse transcription was initiated by adding 0.4 µl of the 25 mM dNTP mix. After incubating at 60° C. for 15 min, the reaction was terminated, processed, and analyzed by electrophoresis in a denaturing 8% TBE-Urea polyacrylamide gel, as described above for template-switching reactions.

Example 3

Further Amino Acid Substitutions into the RT

Figure 16:
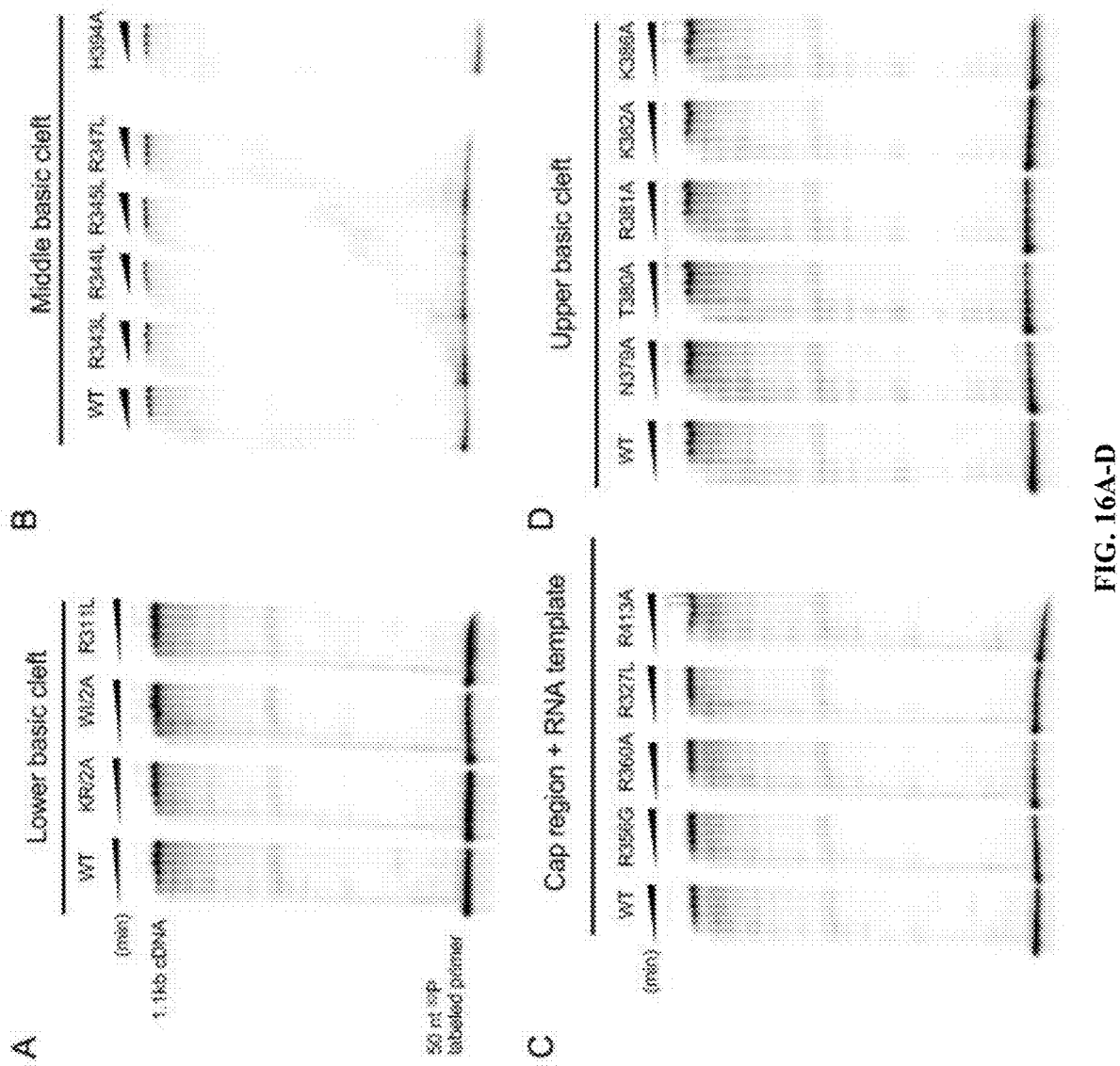

Further studies were undertaken to generate and study additional amino acid substitutions into the surface of the non-LTR-retroelement reverse transcriptase. Details regarding the additional substitutions made are shown in the Table 3 below. Various of the additional substituted RT proteins were further tested to determine effects on protein yield during recombinant expression (FIGS. 13-14, 17) and/or effects on RT activity (FIGS. 15-17).

GsI-IIC RT mutants were expressed as recombinant proteins in *E. coli*, and those that could be expressed were purified and tested for RT activity in primer extension assays. All proteins contain an N-terminal solublity tag (MalE protein) fused to the GsI-IIC RT via a non-cleavable linker (Mohr et al., 2013). In general, all proteins expressed similarly to WT, the only exception was the R311L mutant (FIG. 13). In terms of yield we observed that several mutants increased the total yield of purified protein per L of growth medium. For example, single amino acid substitutions R327L, K322A, R386A, H394A, and K399A increased protein yield about 3- to 4-fold (FIG. 13), and other mutations had more moderate effects. Combinations of individual point mutations resulted in higher protein yield than single mutations. The highest yield (about 10 mg protein per L of growth medium) was achieved for the 3RK/1L5D protein which combines mutations R343L, R381D, K382D, R386D, K389D, and K399D in a single protein. In general, we found that most mutations in GsI-IIC had little or no effect on the amount of soluble protein in soluble cell extracts (FIG. 14).

In addition, we verified that the purified recombinant GsI-IIC RT mutant proteins had RT activity. Since the mutated regions were remote from the RT active site, we expected that thumb and D-domain mutants would not affect RT activity of GsI-IIC RT. To test for RT activity we used a primer extension assay with purified mutant protein and a 1.1-kb RNA template with an annealed DNA primer. Reverse transcription was initiated from a $^{32}$P-labeled 50-nt DNA primer that annealed near the 3' end of RNA. The reaction mixture was incubated at 60° C. in the presence of dNTPs for up to 60 minutes (FIGS. 15, 16A-16D). The results showed that most mutants in the thumb and the D-domain had RT activity comparable to WT GsI-IIC RT.

The GsI-IIC protein has patches of positively charged amino acid residues in the RT fingers and palm domains, such as R58, K160 and K213, R214, and K217. These residues can nonspecifically bind nucleic acids. To reduce this nonspecific binding and to reduce the positive charge, we made two mutants, one having the mutations R58A/K160A and the other having the mutations K213A/R214E/K217A. The R58A/K160A and K213A/R214E/K217A could be concentrated to very high concentrations (12.50 mg/mL and 3.5 mg/mL, respectively) by Amicon centrifugal filtration (FIG. 17, left). K213A/R214E/K217A has primer-extension activity similar to WT, whereas R58A/K160A has a slight reduction in primer-extension activity (FIG. 17, right). The results indicate that the strong positive charge of the GsI-IIC protein's surface is not required for reverse transcriptase activity.

TABLE 3

Further substitutions in a reverse transcriptase of SEQ ID NO: 1.

| Number | Mutants | Plasmid | Assay | Effect |
|---|---|---|---|---|
| 1 | K18A | pMal | Primer extension, Template switching | |
| 2 | K18E | pMal | Primer extension, Template switching, processivity | Processivity defect |
| 3 | R19A | pMal | Primer extension, Template switching, processivity | Processivity defect |
| 4 | R19E | pMal | Primer extension | |
| 5 | R19A/R63A | pMal | Primer extension, Template switching | Template switching defect |
| 6 | R19E/R63E | pMal | Primer extension | |
| 7 | E21A | pMal | Primer extension, Template switching, processivity | Processivity defect |
| 8 | N23A | pMal | Primer extension, Template switching | |
| 9 | I29R | pMal, pDonor | Primer extension, Template switching, Mobility | template switching defect |
| 10 | D30A | pMal | Primer extension, Template switching | |
| 11 | 23-28/6G | pMal | Primer extension, Template switching | template switching defect |
| 12 | 23-31/4G | pMal, pDonor | Primer extension, Template switching, Mobility | Template switching and mobility defect |
| 13 | 23-31/polyG | pMal | Primer extension, Template switching | template switching defect |
| 14 | 23-33/4G | pMal | Primer extension | |
| 15 | N23A/L92A/P112G/R114A/P194G | pMal | Primer extension, Template switching | Primer extension and template switching defect |
| 16 | R63A | pMal, pDonor | Primer extension, Template switching, Mobility | |
| 17 | P68A | pMal, pDonor | Primer extension, Template switching, Mobility | |
| 18 | R85A | pMal, pDonor | Primer extension, Template switching, Mobility | Template switching defect |
| 19 | L92A | pMal | Primer extension | |
| 20 | L92A/N23A | pMal | Primer extension | |
| 21 | P112G | pMal | Primer extension | |
| 22 | P112G/L92A/N23A | pMal | Primer extension, Template switching | |
| 23 | R114A | pMal | Primer extension | |
| 24 | F143A | pMal, pDonor | Primer extension, Template switching, Mobility, nontemplated addition | Template switching, mobility, NTA defect |
| 25 | K141A | pMal | Primer extension | |
| 26 | D144A | pMal, pDonor | Primer extension, Template switching, Mobility, nontemplated addition | |
| 27 | 175-184/polyG | pMal | Primer extension, Template switching | |
| 28 | P194G | pMal | Primer extension | |
| 29 | R291A | pMal | Primer extension | |
| 30 | Q294A | pMal | Primer extension | |
| 31 | R297A | pMal | Primer extension | |
| 32 | Q298A | pMal | Primer extension | |
| 33 | Y318A | pMal | Primer extension, Processivity assay | |
| 34 | Y318A/W322A | pMal | Primer extension | |
| 35 | W322A | pMal | Primer extension | |
| 36 | Y325A | pMal | Primer extension | |
| 37 | Y325F | pMal | Primer extension | |

TABLE 3-continued

Further substitutions in a reverse transcriptase of SEQ ID NO: 1.

| | | | | |
|---|---|---|---|---|
| 38 | F326A | pMal | Primer extension | |
| 39 | F415A | pMal | Primer extension, Template switching | |
| 40 | F415A/P68A | pMal, pDonor | Primer extension, Template switching, Mobility | |
| 41 | YAAA | pDonor | Mobility | Active site defect/control |
| 42 | R58A/K160A | pMal | Primer extension | greatly increased protein yield |
| 43 | K213A/R214E/K217A | pMal | Primer extension | increased protein yield |

| | Mutant | Tested? (Y/N) | NTP or dNTP? | Effect |
|---|---|---|---|---|
| 44 | P68A/F415A | Y | — | In mobility assay showed no effect when compared to WT. |
| 45 | F110A | Y | dNTP | Slightly slower than WT |
| 46 | F142A | N | — | — |
| 47 | F143A | Y | NTP | Incorporated ~4 bases. Essentially no extension |
| 48 | F143V | N | — | — |
| 49 | F143V/Y325V | N | — | — |
| 50 | D144F | Y | dNTP | Slightly slower than WT |
| 51 | Y325A | N | — | — |
| 52 | Y325V | N | — | — |

| | Mutation position | Mutant name | | Effect/ protein yield |
|---|---|---|---|---|
| 53 | Q290A, Q294A, Q298A | 3Q/A | | |
| 54 | K293A, R297A | KR/2A | | |
| 55 | N301H | | | |
| 56 | N303H | | | |
| 57 | N301H, N303H | NN/2H | | |
| 58 | N301H, N303H, S305H, S307H | NNSS/4H | | |
| 59 | N301G, N303G, S305G, S307G | NNSS/4G | | |
| 60 | N301H, N303H, S305H, S307H, Q353R | NNSSQ/4H1R | | |
| 61 | N301H, N303H, S305H, S307H, Q353H | NNSSQ/5H | | |
| 62 | W304A, I306A | WI/A | | |
| 63 | S305H, S307H | SS/2H | | |
| 64 | R311L | | | |
| 65 | R327L | | | increased protein yield |
| 66 | R343L | | | |
| 67 | R343L, K399D | RK/LD | | increased protein yield |
| 68 | R343L, R381D, K382D, K386D, K389D, K399D | 3RK/1L5D | | greatly increased protein yield |
| 69 | R344L | | | |
| 70 | R345L | | | |
| 71 | R344L, R345L | RR/L | | |
| 72 | R347L | | | |
| 73 | Q353H | | | |
| 74 | Q353R | | | |
| 75 | K355D, R356L | KR/DL | | increased protein yield |
| 76 | K355G, R356G, R358A, R360A, R381A, R382A, R386A, K389A | 3K5R/2G6A | | increased protein yield |
| 77 | R356G | | | |
| 78 | R360A | | | |
| 79 | N379A | | | |
| 80 | T380A | | | |

TABLE 3-continued

Further substitutions in a reverse transcriptase of SEQ ID NO: 1.

| | | | |
|---|---|---|---|
| 81 | R381A | | |
| 82 | K382A | | increased protein yield |
| 83 | R386A | | increased protein yield |
| 84 | K389A | | |
| 85 | R381A, K382A | RK/A-1 | |
| 86 | R386A, K389A | RK/A-2 | |
| 87 | R381A, K382A, R386A, K389A | RKRK/A | increased protein yield |
| 88 | R381D, K382A, R386D, K389A | RKRK/DADA | increased protein yield |
| 89 | K399D | | increased protein yield |
| 90 | H394A | | increased protein yield |
| 91 | R413A | | |

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 7,670,807

Adams, P. D., Afonine, P. V., Bunkoczi, G., Chen, V. B., Davis, I. W., Echols, N., Headd, J. J., Hung, L. W., Kapral, G. J., Grosse-Kunstleve, R. W., et al. (2010). PHENIX: a comprehensive Python-based system for macromolecular structure solution. Acta Crystallogr. D Biol. Crystallogr. 66, 213-221.

Aizawa, Y., Xiang, Q., Lambowitz, A.M., and Pyle, A.M. (2003). The pathway for DNA recognition and RNA integration by a group II intron retrotransposon. Mol. Cell 11, 795-805. Appleby, T. C., Perry, J. K., Murakami, E., Barauskas, O., Feng, J., Cho, A., Fox, D., 3rd, Wetmore, D. R., McGrath, M. E., Ray, A. S., et al. (2015). Viral replication. Structural basis for RNA replication by the hepatitis C virus polymerase. Science 347, 771-775. Arnold, J. J., Vignuzzi, M., Stone, J. K., Andino, R., and Cameron, C. E. (2005). Remote site control of an active site fidelity checkpoint in a viral RNA-dependent RNA polymerase. J. Biol. Chem. 280, 25706-25716.

Blocker, F. J. H., Mohr, G., Conlan, L. H., Qi, L., Belfort, M., and Lambowitz, A. M. (2005). Domain structure and three-dimensional model of a group II intron-encoded reverse transcriptase. RNA 11, 14-28.

Bricogne G., Blanc E., Brandl M., Flensburg C., Keller P., Paciorek W., Roversi P, Sharff A., Smart O. S., Vonrhein C., Womack T. O. (2016). BUSTER version 2.10.2. Cambridge, United Kingdom: Global Phasing Ltd.

Carignani, G., Groudinsky, O., Frezza, D., Schiavon, E., Bergantino, E., and Slonimski, P. P. (1983). An mRNA maturase is encoded by the first intron of the mitochondrial gene for the subunit I of cytochrome oxidase in S. cerevisiae. Cell 35, 733-742.

Cavalier-Smith, T. (1991). Intron phylogeny: a new hypothesis. TIG 7, 145-148. Clark, W. C., Evans, M. E., Dominissini, D., Zheng, G., and Pan, T. (2016). tRNA base methylation identification and quantification via high-throughput sequencing. RNA 22, 1771-1784.

Costa, M., Walbott, H., Monachello, D., Westhof, E., and Michel, F. (2016). Crystal structures of a group II intron lariat primed for reverse splicing. Science 354, aaf9258.

Cousineau, B., Smith, D., Lawrence-Cavanagh, S., Mueller, J. E., Yang, J., Mills, D., Manias, D., Dunny, G., Lambowitz, A. M., and Belfort, M. (1998). Retrohoming of a bacterial group II intron: mobility via complete reverse splicing, independent of homologous DNA recombination. Cell 94, 451-462.

Das, K., Martinez, S. E., Bandwar, R. P., and Arnold, E. (2014). Structures of HIV-1 RT-RNA/DNA ternary complexes with dATP and nevirapine reveal conformational flexibility of RNA/DNA: insights into requirements for RNase H cleavage. Nucleic Acids Res. 42, 8125-8137.

Emsley, P., Lohkamp, B., Scott, W. G., and Cowtan, K. (2010). Features and development of Coot. Acta Crystallogr. D Biol. Crystallogr. 66, 486-501.

Evans, P. R., and Murshudov, G. N. (2013). How good are my data and what is the resolution? Acta Crystallogr. D Biol. Crystallogr. 69, 1204-1214.

Fica, S. M., Tuttle, N., Novak, T., Li, N. S., Lu, J., Koodathingal, P., Dai, Q., Staley, J. P., and Piccirilli, J. A. (2013). RNA catalyses nuclear pre-mRNA splicing. Nature 503, 229-234. Fisher, T. S., Darden, T., and Prasad, V. R. (2003). Substitutions at Phe61 in the beta3-beta4 hairpin of HIV-1 reverse transcriptase reveal a role for the Fingers subdomain in strand displacement DNA synthesis. J. Mol. Biol. 325, 443-459.

Galej, W. P., Nguyen, T. H., Newman, A. J., and Nagai, K. (2014). Structural studies of the spliceosome: zooming into the heart of the machine. Curr. Opin. Struct. Biol. 25, 57-66.

Galej, W.P., Oubridge, C., Newman, A. J., and Nagai, K. (2013). Crystal structure of Prp8 reveals active site cavity of the spliceosome. Nature 493, 638-643.

Gao, G., Orlova, M., Georgiadis, M. M., Hendrickson, W. A., and Goff, S. P. (1997). Conferring RNA polymerase activity to a DNA polymerase: a single residue in reverse transcriptase controls substrate selection. *Proc. Natl. Acad. Sci. USA* 94, 407-411.

Gillis, A. J., Schuller, A. P., and Skordalakes, E. (2008). Structure of the Tribolium castaneum telomerase catalytic subunit TERT. Nature 455, 633-637.

Kabsch, W. (2010). Xds. Acta Crystallogr. D Biol. Crystallogr. 66, 125-132.

Kennell, J. C., Moran, J. V., Perlman, P. S., Butow, R. A., and Lambowitz, A. M. (1993). Reverse transcriptase activity associated with maturase-encoding group II introns in yeast mitochondria. Cell 73, 133-146.

Kissinger, C. R., Gehlhaar, D. K., and Fogel, D. B. (1999). Rapid automated molecular replacement by evolutionary search. Acta Crystallogr. D Biol. Crystallogr. 55, 484-491.

Koonin, E. V., Dolja, V. V., and Krupovic, M. (2015). Origins and evolution of viruses of eukaryotes: The ultimate modularity. Virology 479-480, 2-25.

Lambowitz, A., and Belfort, M. (2015). Mobile bacterial group II introns at the crux of eukaryotic evolution. Microbiol. Spectrum 3.

Lambowitz, A. M., and Zimmerly, S. (2011). Group II introns: mobile ribozymes that invade DNA. Cold Spring Harb. Perspect. Biol. 3, a003616.

Malik, H. S., Burke, W. D., Eickbush, T. H. (1999). The age and evolution of non-LTR retrotransposable elements. Mol. Biol. Evol. 16, 793-805.

Marcia, M., and Pyle, A. M. (2012). Visualizing group II intron catalysis through the stages of splicing. Cell 151, 497-507.

Martin, W., and Koonin, E. V. (2006). Introns and the origin of nucleus-cytosol compartmentalization. Nature 440, 41-45.

Michel, F., and Ferat, J. L. (1995). Structure and activities of group II introns. Annu. Rev. Biochem. 64, 435-461.

Mitchell, M., Gillis, A., Futahashi, M., Fujiwara, H., and Skordalakes, E. (2010). Structural basis for telomerase catalytic subunit TERT binding to RNA template and telomeric DNA. Nat. Struct. Mol. Biol. 17, 513-518.

Mohr, S., Ghanem, E., Smith, W., Sheeter, D., Qin, Y., King, O., Polioudakis, D., Iyer, V. R., Hunicke-Smith, S., Swamy, S., et al. (2013). Thermostable group II intron reverse transcriptase fusion proteins and their use in cDNA synthesis and next-generation RNA sequencing. RNA 19, 958-970.

Murshudov, G. N., Skubák, P., Lebedev, A. A., Pannu, N. S., Steiner, R. A., Nicholls, R. A., Winn, M. D., Long, F., and Vagin, A. A. (2011). REFMACS for the refinement of macromolecular crystal structures. Acta Crystallogr. D Biol. Crystallogr. 67, 355-367.

Nguyen, T. H., Galej, W. P., Fica, S. M., Lin, P. C., Newman, A. J., and Nagai, K. (2016). CryoEM structures of two spliceosomal complexes: starter and dessert at the spliceosome feast. Curr. Opin. Struc. Biol. 36, 48-57.

Noah, J. W., Park, S., Whitt, J. T., Perutka, J., Frey, W., and Lambowitz, A. M. (2006). Atomic force microscopy reveals DNA bending during group II intron ribonucleoprotein particle integration into double-stranded DNA. Biochemistry 45, 12424-12435.

Nottingham, R. M., Wu, D. C., Qin, Y., Yao, J., Hunicke-Smith, S., and Lambowitz, A.M. (2016). RNA-seq of human reference RNA samples using a thermostable group II intron reverse transcriptase. RNA 22, 597-613.

Paukstelis, P. J., Chen, J. H., Chase, E., Lambowitz, A. M., and Golden, B. L. (2008). Structure of a tyrosyl-tRNA synthetase splicing factor bound to a group I intron RNA. Nature 451, 94-97.

Peebles, C. L., Perlman, P. S., Mecklenburg, K. L., Petrillo, M. L., Tabor, J. H., Jarrell, K. A., and Cheng, H. L. (1986). A self-splicing RNA excises an intron lariat. Cell 44, 213-223.

Qu, G., Kaushal, P. S., Wang, J., Shigematsu, H., Piazza, C. L., Agrawal, R. K., Belfort, M., and Wang, H. W. (2016). Structure of a group II intron in complex with its reverse transcriptase. Nat. Struct. Mol. Biol. 23, 549-557.

Saldanha, R., Chen, B., Wank, H., Matsuura, M., Edwards, J., and Lambowitz, A. M. (1999). RNA and protein catalysis in group II intron splicing and mobility reactions using purified components. Biochemistry 38, 9069-9083.

San Filippo, J., and Lambowitz, A. M. (2002). Characterization of the C-terminal DNA-binding/DNA endonuclease region of a group II intron-encoded protein. J. Mol. Biol. 324, 933-951.

Sawaya, M. R., Prasad, R., Wilson, S. H., Kraut, J., and Pelletier, H. (1997). Crystal structures of human DNA polymerase beta complexed with gapped and nicked DNA: evidence for an induced fit mechanism. Biochemistry 36, 11205-11215.

Sharp, P. A. (1985). On the origin of RNA splicing and introns. Cell 42, 397-400.

Sontheimer, E. J., Gordon, P. M., and Piccirilli, J. A. (1999). Metal ion catalysis during group II intron self-splicing: parallels with the spliceosome. Genes Dev. 13, 1729-1741.

Toro, N., Nisa-Martínez, R. (2014). Comprehensive phylogenetic analysis of bacterial reverse transcriptases. PLoS ONE 9, e114083.

Wang, H., and Lambowitz, A. M. (1993). The Mauriceville plasmid reverse transcriptase can initiate cDNA synthesis de novo and may be related to reverse transcriptase and DNA polymerase progenitor. Cell 75, 1071-1081.

Wu, X., and Bartel, D.P. (2017). Widespread influence of 3'-end structures on mammalian mRNA processing and stability. Cell 169, 905-917 e911.

Yang, J., Zimmerly, S., Perlman, P. S., and Lambowitz, A. M. (1996). Efficient integration of an intron RNA into double-stranded DNA by reverse splicing. Nature 381, 332-335.

Zhao, C., and Pyle, A. M. (2016). Crystal structures of a group II intron maturase reveal a missing link in spliceosome evolution. Nat. Struct. Mol. Biol. 23, 558-565.

Zheng, G., Qin, Y., Clark, W. C., Dai, Q., Yi, C., He, C., Lambowitz, A. M., and Pan, T. (2015). Efficient and quantitative high-throughput tRNA sequencing. Nat. Methods 12, 835-837.

Zimmerly, S., Guo, H., Eskes, R., Yang, J., Perlman, P. S., and Lambowitz, A. M. (1995a). A group II intron RNA is a catalytic component of a DNA endonuclease involved in intron mobility. Cell 83, 529-538.

Zimmerly, S., Guo, H., Perlman, P. S., and Lambowitz, A. M. (1995b). Group II intron mobility occurs by target DNA-primed reverse transcription. Cell 82, 545-554.

Zimmerly, S., Wu, L. (2015). An unexplored diversity of reverse transcriptases in bacteria. Microbiol. Spectr. 3, 1253-1269.

Zubradt, M., Gupta, P., Persad, S., Lambowitz, A. M., Weissman, J. S., and Rouskin, S. (2016). DMS-MaPseq for genome-wide or targeted RNA structure probing in vivo. Nat. Methods 14, 75-82.

What is claimed is:

1. A non-LTR-retroelement reverse transcriptase (RT) comprising an amino acid sequence having at least 85% sequence identity to SEQ ID NO: 1, wherein said reverse transcriptase comprises an amino acid substitution at an amino acid position corresponding to R58, F143, K160, R214, R343, R381, K382, R386, K389, H394 or K399, that (a) contacts a template nucleic acid, a primer oligonucleotide, and/or an incoming dNTP; or (b) is on the surface of the non-LTR-retroelement reverse transcriptase.

2. The non-LTR-retroelement reverse transcriptase of claim 1, comprising an amino acid substitution at an amino acid position corresponding to a position of SEQ ID NO: 1 that (a) contacts a template nucleic acid, a primer oligonucleotide and/or an incoming dNTP.

3. The non-LTR-retroelement reverse transcriptase of claim 2, wherein the amino acid position that contacts a template nucleic acid, a primer oligonucleotide and/or an incoming dNTP is identified as such based on a crystal comprising a substantially pure non-LTR-retroelement reverse transcriptase comprised of at least a reverse transcriptase and a thumb domain in complex with template and primer oligonucleotide and incoming dNTP, wherein the non-LTR-retroelement reverse transcriptase has at least 95% sequence identity to SEQ ID NO: 1, and wherein the crystal has a space group of C 1 2 1.

4. The non-LTR-retroelement reverse transcriptase of claim 1, wherein the non-LTR-retroelement reverse transcriptase further comprises an amino acid substitution at a position or set of positions selected from the group consisting of: (i) N23; (ii) N23, Q24, G25, A26, P27, G28, I29, D30, and G31; (iii) I29; (iv) R63; (v) L77 and I79; and (vi) R85.

5. The non-LTR-retroelement reverse transcriptase of claim 4, wherein the amino acid substitution is at a substitution or set of substitutions selected from the group consisting of:
  (i) N23A;
  (ii) replacement of the set of residues N23, Q24, G25, A26, P27, G28, I29, D30, and G31 with GGGG;

(iii) I29R;
(iv) R63A;
(v) L77A and I79A;
(vi) R85A; and
(vii) F143A.

6. The non-LTR-retroelement reverse transcriptase of claim 1, comprising an amino acid substitution at an amino acid position corresponding to a position of SEQ ID NO: 1 that (b) is on the surface of the non-LTR-retroelement reverse transcriptase.

7. The non-LTR-retroelement reverse transcriptase of claim 6, wherein the amino acid position that is on the surface of the RT is identified as such based on a crystal comprising a substantially pure non-LTR-retroelement reverse transcriptase comprised of at least a reverse transcriptase and a thumb domain in complex with template and primer oligonucleotide and incoming dNTP, wherein the non-LTR-retroelement reverse transcriptase has at least 95% sequence identity to SEQ ID NO: 1, and wherein the crystal has a space group of C 1 2 1.

8. The non-LTR-retroelement reverse transcriptase of claim 6, wherein the amino acid substitutions is at a position that does not contact a template nucleic acid, a primer oligonucleotide, and/or an incoming dNTP.

9. The non-LTR-retroelement reverse transcriptase of claim 6, wherein the non-LTR-retroelement reverse transcriptase further comprises an amino acid substitution at a position or set of positions selected from the group consisting of: (i) K213 and K217; (ii) Q290, Q294, and Q298; (iii) K293 and R297; (iv) K327; (v) K339; (vi) R345; (vii) R360; and (viii) R413.

10. The non-LTR-retroelement reverse transcriptase of claim 1, wherein the non-LTR-retroelement reverse transcriptase comprises: increased or decreased template switching activity; increased or decreased processivity; increased or decreased strand displacement activity; or increased or decreased fidelity.

11. The non-LTR-retroelement reverse transcriptase of claim 1, wherein the non-LTR-retroelement reverse transcriptase comprises increased or decreased template switching activity; increased processivity; increased strand displacement activity; or increased fidelity.

12. The non-LTR-retroelement reverse transcriptase of claim 1, wherein the non-LTR-retroelement reverse transcriptase comprises: improved stability, improved solubility, decreased non-specific nucleic acid binding or improved ability to be purified.

13. The non-LTR-retroelement reverse transcriptase of claim 1, wherein the non-LTR-retroelement reverse transcriptase exhibits increased yield during recombinant production.

14. The non-LTR-retroelement reverse transcriptase of claim 1, wherein the non-LTR-retroelement reverse transcriptase comprises a bacterial reverse transcriptase.

15. The non-LTR-retroelement reverse transcriptase of claim 1, wherein the non-LTR-retroelement reverse transcriptase comprises a group II intron reverse transcriptase.

16. The non-LTR-retroelement reverse transcriptase of claim 1, wherein the non-LTR-retroelement reverse transcriptase further comprises a stability tag.

17. The non-LTR-retroelement reverse transcriptase of claim 16, wherein the stability tag comprises MalE.

18. A method for reverse transcribing a template comprising contacting the template with THE non-LTR-retroelement reverse transcriptase (RT) in accordance with claim 1 under conditions permissible for reverse transcription.

19. A kit comprising THE non-LTR-retroelement reverse transcriptase (RT) in accordance with claim 1.

20. The non-LTR-retroelement reverse transcriptase of claim 9, wherein the amino acid substitution is at a set of positions selected from the group consisting of: (i) R58 and K160; (ii) K213, R214 and K217; (iii) R343 and K339; (iv) R343, R381, K382, R386, K389, and K399; and (v) R381, K382, R386, and K389.

21. The non-LTR-retroelement reverse transcriptase of claim 20, wherein the amino acid substitution is at a substitution or set of substitutions selected from the group consisting of:
(i) R58A and K160A;
(ii) K213A, R214E, and K217A;
(iii) Q290A, Q294A, and Q298A;
(iv) K293A and R297A;
(v) R327L;
(vi) R343L;
(vii) R343L and K339D;
(viii) R343L, R381D, K382D, R386D, K389D, and K399D;
(ix) R345L;
(x) R360A;
(xi) R381A;
(xii) R381A/D, K382A, R386A/D, and K389A;
(xiii) K382A;
(xiv) R386A; and
(xv) R413A.

* * * * *

UNITED STATES PATENT AND TRADEMARK OFFICE
CERTIFICATE OF CORRECTION

PATENT NO. : 12,203,107 B2
APPLICATION NO. : 17/741437
DATED : January 21, 2025
INVENTOR(S) : Jennifer L. Stamos et al.

It is certified that error appears in the above-identified patent and that said Letters Patent is hereby corrected as shown below:

In the Claims

In Claim 18, Column 50, Line 16, delete "THE" and insert --the-- therefor.

In Claim 19, Column 50, Line 19, delete "THE" and insert --the-- therefor.

Signed and Sealed this
Twenty-seventh Day of May, 2025

Coke Morgan Stewart
*Acting Director of the United States Patent and Trademark Office*

SEQUENCE LISTING

<160> NUMBER OF SEQ ID NOS: 34

<210> SEQ ID NO 1
<211> LENGTH: 420
<212> TYPE: PRT
<213> ORGANISM: Geobacillus stearothermophilus

<400> SEQUENCE: 1

```
Met Ala Leu Leu Glu Arg Ile Leu Ala Arg Asp Asn Leu Ile Thr Ala
1               5                   10                  15

Leu Lys Arg Val Glu Ala Asn Gln Gly Ala Pro Gly Ile Asp Gly Val
            20                  25                  30

Ser Thr Asp Gln Leu Arg Asp Tyr Ile Arg Ala His Trp Ser Thr Ile
        35                  40                  45

His Ala Gln Leu Leu Ala Gly Thr Tyr Arg Pro Ala Pro Val Arg Arg
    50                  55                  60

Val Glu Ile Pro Lys Pro Gly Gly Thr Arg Gln Leu Gly Ile Pro
65                  70                  75                  80

Thr Val Val Asp Arg Leu Ile Gln Gln Ala Ile Leu Gln Glu Leu Thr
                85                  90                  95

Pro Ile Phe Asp Pro Asp Phe Ser Ser Ser Phe Gly Phe Arg Pro
            100                 105                 110

Gly Arg Asn Ala His Asp Ala Val Arg Gln Ala Gln Gly Tyr Ile Gln
            115                 120                 125

Glu Gly Tyr Arg Tyr Val Val Asp Met Asp Leu Glu Lys Phe Phe Asp
        130                 135                 140

Arg Val Asn His Asp Ile Leu Met Ser Arg Val Ala Arg Lys Val Lys
145                 150                 155                 160

Asp Lys Arg Val Leu Lys Leu Ile Arg Ala Tyr Leu Gln Ala Gly Val
                165                 170                 175

Met Ile Glu Gly Val Lys Val Gln Thr Glu Glu Gly Thr Pro Gln Gly
            180                 185                 190

Gly Pro Leu Ser Pro Leu Leu Ala Asn Ile Leu Leu Asp Asp Leu Asp
        195                 200                 205

Lys Glu Leu Glu Lys Arg Gly Leu Lys Phe Cys Arg Tyr Ala Asp Asp
    210                 215                 220

Cys Asn Ile Tyr Val Lys Ser Leu Arg Ala Gly Gln Arg Val Lys Gln
225                 230                 235                 240

Ser Ile Gln Arg Phe Leu Glu Lys Thr Leu Lys Leu Lys Val Asn Glu
                245                 250                 255

Glu Lys Ser Ala Val Asp Arg Pro Trp Lys Arg Ala Phe Leu Gly Phe
            260                 265                 270

Ser Phe Thr Pro Glu Arg Lys Ala Arg Ile Arg Leu Ala Pro Arg Ser
        275                 280                 285

Ile Gln Arg Leu Lys Gln Arg Ile Arg Gln Leu Thr Asn Pro Asn Trp
    290                 295                 300

Ser Ile Ser Met Pro Glu Arg Ile His Arg Val Asn Gln Tyr Val Met
305                 310                 315                 320

Gly Trp Ile Gly Tyr Phe Arg Leu Val Glu Thr Pro Ser Val Leu Gln
                325                 330                 335

Thr Ile Glu Gly Trp Ile Arg Arg Leu Arg Leu Cys Gln Trp Leu
            340                 345                 350

Gln Trp Lys Arg Val Arg Thr Arg Ile Arg Glu Leu Arg Ala Leu Gly
        355                 360                 365
```

```
Leu Lys Glu Thr Ala Val Met Glu Ile Ala Asn Thr Arg Lys Gly Ala
    370                 375                 380

Trp Arg Thr Thr Lys Thr Pro Gln Leu His Gln Ala Leu Gly Lys Thr
385                 390                 395                 400

Tyr Trp Thr Ala Gln Gly Leu Lys Ser Leu Thr Gln Arg Tyr Phe Glu
                405                 410                 415

Leu Arg Gln Gly
            420

<210> SEQ ID NO 2
<211> LENGTH: 50
<212> TYPE: DNA
<213> ORGANISM: Artificial sequence
<220> FEATURE:
<223> OTHER INFORMATION: Synthetic primer

<400> SEQUENCE: 2
tcttcggggc gaaaactctc aaggatctta ccgctgttga gatccagttc          50

<210> SEQ ID NO 3
<211> LENGTH: 35
<212> TYPE: DNA
<213> ORGANISM: Artificial sequence
<220> FEATURE:
<223> OTHER INFORMATION: Synthetic primer

<400> SEQUENCE: 3
gtgactggag ttcagacgtg tgctcttccg atctg                          35

<210> SEQ ID NO 4
<211> LENGTH: 34
<212> TYPE: RNA
<213> ORGANISM: Artificial sequence
<220> FEATURE:
<223> OTHER INFORMATION: Synthetic primer
<220> FEATURE:
<221> NAME/KEY: misc_feature
<222> LOCATION: (1)..(34)
<223> OTHER INFORMATION: ribosomal RNA

<400> SEQUENCE: 4
agaucggaag agcacacguc ugaacuccag ucac                           34

<210> SEQ ID NO 5
<211> LENGTH: 50
<212> TYPE: RNA
<213> ORGANISM: Artificial sequence
<220> FEATURE:
<223> OTHER INFORMATION: Synthetic primer
<220> FEATURE:
<221> NAME/KEY: misc_feature
<222> LOCATION: (1)..(50)
<223> OTHER INFORMATION: ribosomal RNA

<400> SEQUENCE: 5
cgccggaccg ugcaccaucu ggaguuauag agaugagucu cacauagacc          50

<210> SEQ ID NO 6
<211> LENGTH: 56
<212> TYPE: DNA
<213> ORGANISM: Artificial sequence
<220> FEATURE:
<223> OTHER INFORMATION: Synthetic primer

<400> SEQUENCE: 6
ggcggcggca tcggcggcgg catcgacgga gtatcaaccg gacggagtat caaccg   56
```

<210> SEQ ID NO 7
<211> LENGTH: 27
<212> TYPE: DNA
<213> ORGANISM: Artificial sequence
<220> FEATURE:
<223> OTHER INFORMATION: Synthetic primer

<400> SEQUENCE: 7
gccgccgccg gcttcgaccc gtttgag                                27

<210> SEQ ID NO 8
<211> LENGTH: 26
<212> TYPE: DNA
<213> ORGANISM: Artificial sequence
<220> FEATURE:
<223> OTHER INFORMATION: Synthetic primer

<400> SEQUENCE: 8
ggcggcgtat caaccgatca actccg                                 26

<210> SEQ ID NO 9
<211> LENGTH: 24
<212> TYPE: DNA
<213> ORGANISM: Artificial sequence
<220> FEATURE:
<223> OTHER INFORMATION: Synthetic primer

<400> SEQUENCE: 9
gccgccggct tcgacccgtt tgag                                   24

<210> SEQ ID NO 10
<211> LENGTH: 28
<212> TYPE: DNA
<213> ORGANISM: Artificial sequence
<220> FEATURE:
<223> OTHER INFORMATION: Synthetic primer

<400> SEQUENCE: 10
agcaccggga cgagacggag tatcaacc                               28

<210> SEQ ID NO 11
<211> LENGTH: 18
<212> TYPE: DNA
<213> ORGANISM: Artificial sequence
<220> FEATURE:
<223> OTHER INFORMATION: Synthetic primer

<400> SEQUENCE: 11
ccttggttgg cttcgacc                                          18

<210> SEQ ID NO 12
<211> LENGTH: 25
<212> TYPE: DNA
<213> ORGANISM: Artificial sequence
<220> FEATURE:
<223> OTHER INFORMATION: Synthetic primer

<400> SEQUENCE: 12
accgggaatc gctggagtat caacc                                  25

<210> SEQ ID NO 13
<211> LENGTH: 18
<212> TYPE: DNA
<213> ORGANISM: Artificial sequence
<220> FEATURE:

```
<223> OTHER INFORMATION: Synthetic primer

<400> SEQUENCE: 13
gctccttggt tggcttcg                                                    18

<210> SEQ ID NO 14
<211> LENGTH: 27
<212> TYPE: DNA
<213> ORGANISM: Artificial sequence
<220> FEATURE:
<223> OTHER INFORMATION: Synthetic primer

<400> SEQUENCE: 14
cgtggtggac gcactgatcc aacaagc                                          27

<210> SEQ ID NO 15
<211> LENGTH: 18
<212> TYPE: DNA
<213> ORGANISM: Artificial sequence
<220> FEATURE:
<223> OTHER INFORMATION: Synthetic primer

<400> SEQUENCE: 15
gtgggaatgc ctagctgc                                                    18

<210> SEQ ID NO 16
<211> LENGTH: 4
<212> TYPE: PRT
<213> ORGANISM: Artificial sequence
<220> FEATURE:
<223> OTHER INFORMATION: Synthetic peptide

<400> SEQUENCE: 16

Tyr Ala Asp Asp
1

<210> SEQ ID NO 17
<211> LENGTH: 5
<212> TYPE: PRT
<213> ORGANISM: Artificial sequence
<220> FEATURE:
<223> OTHER INFORMATION: Synthetic peptide

<400> SEQUENCE: 17

Gly Trp Ile Gly Tyr
1               5

<210> SEQ ID NO 18
<211> LENGTH: 5
<212> TYPE: PRT
<213> ORGANISM: Artificial sequence
<220> FEATURE:
<223> OTHER INFORMATION: Synthetic peptide

<400> SEQUENCE: 18

Gly Ile Cys Asn Tyr
1               5

<210> SEQ ID NO 19
<211> LENGTH: 4
<212> TYPE: PRT
<213> ORGANISM: Artificial sequence
<220> FEATURE:
<223> OTHER INFORMATION: Synthetic peptide

<400> SEQUENCE: 19
```

```
Tyr Met Asp Asp
1

<210> SEQ ID NO 20
<211> LENGTH: 5
<212> TYPE: PRT
<213> ORGANISM: Artificial sequence
<220> FEATURE:
<223> OTHER INFORMATION: Synthetic peptide

<400> SEQUENCE: 20

Gly Lys Leu Asn Trp
1               5

<210> SEQ ID NO 21
<211> LENGTH: 4
<212> TYPE: PRT
<213> ORGANISM: Artificial sequence
<220> FEATURE:
<223> OTHER INFORMATION: Synthetic peptide

<400> SEQUENCE: 21

Thr Val Asp Asp
1

<210> SEQ ID NO 22
<211> LENGTH: 4
<212> TYPE: PRT
<213> ORGANISM: Artificial sequence
<220> FEATURE:
<223> OTHER INFORMATION: Synthetic peptide

<400> SEQUENCE: 22

Phe Ala Asp Asp
1

<210> SEQ ID NO 23
<211> LENGTH: 5
<212> TYPE: PRT
<213> ORGANISM: Artificial sequence
<220> FEATURE:
<223> OTHER INFORMATION: Synthetic peptide

<400> SEQUENCE: 23

Pro Lys Val Ile Tyr
1               5

<210> SEQ ID NO 24
<211> LENGTH: 5
<212> TYPE: PRT
<213> ORGANISM: Artificial sequence
<220> FEATURE:
<223> OTHER INFORMATION: Synthetic peptide

<400> SEQUENCE: 24

Pro Arg Phe Gln His
1               5

<210> SEQ ID NO 25
<211> LENGTH: 4
<212> TYPE: PRT
<213> ORGANISM: Artificial sequence
<220> FEATURE:
<223> OTHER INFORMATION: Synthetic peptide

<400> SEQUENCE: 25

Tyr Leu Asp Arg
```

<210> SEQ ID NO 26
<211> LENGTH: 5
<212> TYPE: PRT
<213> ORGANISM: Artificial sequence
<220> FEATURE:
<223> OTHER INFORMATION: Synthetic peptide

<400> SEQUENCE: 26

Ser Leu Phe Thr Tyr
1               5

<210> SEQ ID NO 27
<211> LENGTH: 4
<212> TYPE: PRT
<213> ORGANISM: Artificial sequence
<220> FEATURE:
<223> OTHER INFORMATION: Synthetic peptide

<400> SEQUENCE: 27

Cys Gly Asp Asp
1

<210> SEQ ID NO 28
<211> LENGTH: 11
<212> TYPE: DNA
<213> ORGANISM: Artificial sequence
<220> FEATURE:
<223> OTHER INFORMATION: Synthetic primer

<400> SEQUENCE: 28
caacggacct c                                                            11

<210> SEQ ID NO 29
<211> LENGTH: 14
<212> TYPE: RNA
<213> ORGANISM: Artificial sequence
<220> FEATURE:
<223> OTHER INFORMATION: Synthetic oligo

<400> SEQUENCE: 29
gagguccguu guuu                                                         14

<210> SEQ ID NO 30
<211> LENGTH: 114
<212> TYPE: PRT
<213> ORGANISM: Artificial sequence
<220> FEATURE:
<223> OTHER INFORMATION: Synthetic peptide

<400> SEQUENCE: 30

Pro Arg Ser Ile Gln Arg Leu Lys Gln Arg Ile Arg Gln Leu Thr Asn
1               5                   10                  15

Pro Asn Trp Ser Ile Ser Met Pro Glu Arg Ile His Arg Val Asn Gln
            20                  25                  30

Tyr Val Met Gly Trp Ile Gly Tyr Phe Arg Leu Val Glu Thr Pro Ser
        35                  40                  45

Val Leu Gln Thr Ile Glu Gly Trp Ile Arg Arg Leu Arg Leu Cys
    50                  55                  60

Gln Trp Leu Gln Trp Lys Arg Val Thr Thr Arg Ile Arg Glu Leu Arg
65                  70                  75                  80

Ala Leu Gly Leu Lys Glu Thr Ala Val Met Glu Ile Ala Asn Thr Arg
                85                  90                  95

```
Lys Gly Ala Trp Arg Thr Thr Lys Thr Pro Gln Leu Gly Gln Ala Leu
            100                 105                 110
Gly Lys

<210> SEQ ID NO 31
<211> LENGTH: 11
<212> TYPE: DNA
<213> ORGANISM: Artificial sequence
<220> FEATURE:
<223> OTHER INFORMATION: Synthetic primer

<400> SEQUENCE: 31
caacggacct c                                                          11

<210> SEQ ID NO 32
<211> LENGTH: 14
<212> TYPE: RNA
<213> ORGANISM: Artificial sequence
<220> FEATURE:
<223> OTHER INFORMATION: Synthetic oligo

<400> SEQUENCE: 32
gagguccguu guuu                                                       14

<210> SEQ ID NO 33
<211> LENGTH: 13
<212> TYPE: DNA
<213> ORGANISM: Artificial sequence
<220> FEATURE:
<223> OTHER INFORMATION: Synthetic oligo

<400> SEQUENCE: 33
caacggacct ctg                                                        13

<210> SEQ ID NO 34
<211> LENGTH: 14
<212> TYPE: RNA
<213> ORGANISM: Artificial sequence
<220> FEATURE:
<223> OTHER INFORMATION: Synthetic oligo

<400> SEQUENCE: 34
cagagguccg uugu                                                       14
```